US009429574B2

(12) United States Patent
Nuber

(10) Patent No.: US 9,429,574 B2
(45) Date of Patent: Aug. 30, 2016

(54) CANCER THERAPIES AND METHODS

(71) Applicant: Ulrike Nuber, Malmö (SE)

(72) Inventor: Ulrike Nuber, Malmo (SE)

( * ) Notice: Subject to any disclaimer, the term of this patent is extended or adjusted under 35 U.S.C. 154(b) by 0 days.

(21) Appl. No.: 13/683,179

(22) Filed: Nov. 21, 2012

(65) Prior Publication Data

US 2014/0179618 A1    Jun. 26, 2014

Related U.S. Application Data

(63) Continuation-in-part of application No. PCT/EP2012/059160, filed on May 16, 2012.

(30) Foreign Application Priority Data

May 16, 2011 (GB) .................................. 1108085.0
Feb. 21, 2012 (GB) .................................. 1202945.0

(51) Int. Cl.

| | | |
|---|---|---|
| *A61K 38/00* | (2006.01) | |
| *G01N 33/00* | (2006.01) | |
| *C07K 16/00* | (2006.01) | |
| *G01N 33/574* | (2006.01) | |
| *A61K 31/69* | (2006.01) | |
| *A61K 45/06* | (2006.01) | |
| *A61K 31/353* | (2006.01) | |
| *A61K 31/5377* | (2006.01) | |
| *A61K 38/06* | (2006.01) | |

(52) U.S. Cl.
CPC ........... *G01N 33/574* (2013.01); *A61K 31/353* (2013.01); *A61K 31/5377* (2013.01); *A61K 31/69* (2013.01); *A61K 38/06* (2013.01); *A61K 45/06* (2013.01)

(58) Field of Classification Search
None
See application file for complete search history.

(56) References Cited

U.S. PATENT DOCUMENTS

2006/0084691 A1    4/2006    Piperdi
2009/0131367 A1*   5/2009    Gore et al. ................ 514/64
2010/0113392 A1    5/2010    Badros

FOREIGN PATENT DOCUMENTS

WO    2010039762 A2    4/2010
WO    WO-2012156463 A1    11/2012

OTHER PUBLICATIONS

Roberts, The Role of SMARCB1/INI1 in the Development of Rhabdoid Tumors Cancer Biology and Therapy 8:5, 412-414: Mar. 2009.*
Myung, Med Res Rev. Jul. 2001; 21(4): 245-273.*
Geradts, Mod Pathol 2001;14(11):1162-1168.*
Fester, Karin, Mar. 2010, Plant Alkaloids. In: eLS. John Wiley & Sons Ltd, Chichester. http://www.els.net.*
M. Esteller, "Epigenetics provides a new generation of oncogenes and tumour-suppressor genes", British Journal of Cancer, vol. 94, pp. 179-183 (2006).
F. Bourdeaut et al., "Frequent hSNF5/INI1 Germline Mutations in Patients with Rhabdoid Tumor", Clinical Cancer Research, 17(1), pp. 31-38 (2011).
M. Bi et al., "ER stress-regulated translation increases tolerance to extreme hypoxia and promotes tumor growth", The EMBO Journal, 24(19), pp. 3470-3481 (2005).
H.P. Harding et al., "An Integrated Stress Response Regulates Amino Acid Metabolism and Resistance to Oxidative Stress", Molecular Cell, vol. 11, pp. 619-633 (2003).
C. Koumenis et al., "Regulation of Protein Synthesis by Hypoxia via Activation of the Endoplasmic Reticulum Kinase PERK and Phosphorylation of the Translation Initiation Factor eIF2alpha", Molecular and Cellular Biology, 22(21), pp. 7405-7416 (2002).
H. Muaddi et al., "Phosphorylation of eIF2alpha at Serine 51 Is an Important Determinant of Cell Survival and Adaptation to Glucose Deficiency", Molecular Biology of the Cell, vol. 21, pp. 3220-3231 (2010).
D.M. Schewe et al., "Inhibition of eIF2alpha Dephosphorylation Maximizes Bortezomib Efficiency and Eliminates Quiescent Multiple Myeloma Cells Surviving Proteasome Inhibitor Therapy", Cancer Research, 69(4), pp. 1545-1552 (2009).
P. van den Munckhof et al., "Germline SMARCB1 mutation predisposes to multiple meningiomas and schwannomas with preferential location of cranial meningiomas at the falx cerebri", Neurogenetics,vol. 13, pp. 1-7 (2012).
I. Versteege et al., "Truncating mutations of hSNF5/INI1 in aggressive paediatric cancer", Nature, vol. 394, pp. 203-206 (1998).
R.L. Wiseman et al., "A new pharmacology-drugging stressed folding pathways", Trends in Molecular Medicine, 11 (8), pp. 347-350 (2005).
D.Y. Wu et al., "The Human SNF5/INI1 Protein Facilitates the Function of the Growth Arrest and DNA Damage-inducible Protein (GADD34) and Modulates GADD34-bound Protein Phosphatase-1 Activity", The Journal of Biological Chemistry, 277(31), pp. 27706-27715 (2002).
Y. Xu et al., "SNF5, a core component of the SWI/SNF complex, is necessary for p53 expression and cell survival, in part through eIF4E", Oncogene, vol. 29, pp. 4090-4100 (2010).

(Continued)

*Primary Examiner* — Jeanette Lieb
(74) *Attorney, Agent, or Firm* — Foley & Lardner LLP

(57) ABSTRACT

The present invention provides an inhibitor of the ubiquitin-proteasome system for use in treating cancer in a patient, wherein the patient is assessed to establish that the cancer is associated with cells in which the functional activity of SMARCB1 is low or absent. In one embodiment, the patient has, or is suspected of having, breast cancer, an atypical teratoid rhabdoid tumor (AT/RT) and/or a malignant rhabdoid tumor (MRT). In one embodiment, the proteasome inhibitor is Bortezomib. Further aspects of the invention provide related uses and methods.

26 Claims, 2 Drawing Sheets

(56) References Cited

OTHER PUBLICATIONS

Charles W. M. Roberts et al., "The role of SMARCB1/INI1 in development of rhabdoid tumor", Cancer Biology & Therapy, Landes Bioscience, vol. 8, Issue 5, pp. 412-416 (Mar. 2009).
Aaron Ciechanover, "The ubiquitin-proteasome pathway: on protein death and cell life", European Molecular Biology Corporation, Members Review, vol. 17, No. 24, pp. 7151-7160 (1998).
Lynn Bedford et al., "Ubiquitin-like protein conjugation and the ubiquitin-proteasome system as drug targets", Nature Reviews/Drug Discovery, vol. 10, pp. 29-46 (Jan. 2011).
Geoffroy de Bettignies et al., "Proteasome inhibitors: Dozens of molecules and still counting", Biochimie, vol. 92, pp. 1530-1545(2010).
Haskell T. Adler, "Leukemic HRX Fusion Proteins Inhibit GADD34-Induced Apoptosis and Associate with the GADD34 and hSNF5/INI1 Proteins", Molecular and Cellular Biology, vol. 19, No. 10, pp. 7050-7060.
Kenichi Kohashi et al., "Reduced expression of SMARCB1/INI1 protein in synovial sarcoma", Modern Pathology, vol. 23, pp. 981-990 (2010).
Nicholas Sevenet et al., "Constitutional Mutations of the hSNF5/INI1 Gene Predispose to a Variety of Cancers", American Journal of Human Genetics, vol. 65, pp. 1342-1348 (1999).
Katherin W. Eaton et al., "Spectrum of SMARCB1/INI1 Mutations in Familial and Sporadic Rhabdoid Tumors", Pediatr Blood Cancer, vol. 56, pp. 7-15 (2011).
M. Esteller, "Epigenetics provides a new generation of oncogenes and tumour-suppressor genes", British Journal of Cancer, vol. 94, pp. 179-183 (2004).
Kenichi Kohashi et al., "Infrequent SMARCB1/INI1 gene alteration in apithelioid sarcoma: a useful tool in distinguishing epithelioid sarcoma from malignant rhabdoid tumor", Human Pathology, vol. 40, pp. 349-355 (2009).
Hironori Fujisawa et al., Cyclin D1 is overexpressed in atypical teratoid/rhabdoid tumor with hSNF5/INI1 gene inactivation, Journal of Neuro-Oncology, vol. 73, pp. 117-124 (2005).
Jim Kling, "New twists on proteasome inhibitors", Nature Biotechnology, vol. 28, No. 12, pp. 1236-1238 (Dec. 2010).
Alfonso Gennaro, Remington: The Science and Practice of Pharmacy, 19th edition (1995), Mack Publishing Company, Pennsylvania USA (entire book).
Bersani et al., "Bortezomib-mediated proteasome inhibition as a potential strategy for the treatment of rhabdomyosarcoma," European Journal of Cancer, vol. 44, pp. 876-884, Mar. 2008.
Yuehua, "Progress in Research on Action Mechanism, Clinical Application and Efficacy of Bortezomib", Journal of Practical Diagnosis and Therapy, vol. 22, No. 4, Dec. 31, 2008.
Chinese Office Action issued in application No. 201280023500.6 on Oct. 29, 2015.

* cited by examiner

CANCER THERAPIES AND METHODS

This application is a Continuation-in-Part of International Application PCT/EP2012/059160 having an International filing date of May 16, 2012, which claims under 35 U.S.C. §119(a) the benefit of Great Britain Application No. 1202945.0, filed Feb. 21, 2012 and Great Britain Application No.: 1108085.0, filed May 16, 2011, the entire contents of each applications is incorporated herein by reference.

FIELD OF INVENTION

The present invention relates to novel therapies and methods for the treatment of cancer in a patient. In particular, there are provided agents and methods for use in the treatment of cancer wherein the level of functional activity of SMARCB1 in the cancer cells is used to determine whether the patient would benefit from treatment with an inhibitor of the ubiquitin-proteasome system.

BACKGROUND

Rhabdoid tumors are lethal cancers that predominantly strike young children. The vast majority of rhabdoid tumors contain bi-allelic inactivating mutations in the SMARCB1 gene (see Roberts & Biegel, 2009, Cancer Biol. Ther. 8(5), 412-416).

Rhabdoid tumors are highly malignant neoplasms that typically arise in infancy and early childhood. The tumors develop in the brain and spinal cord [referred to as atypical teratoid/rhabdoid tumor (AT/RT)], kidney and/or soft tissues (termed malignant rhabdoid tumor or extra-renal rhabdoid tumor). The histologic appearance of these malignancies can be quite variable. Most tumors contain at least some fields with classic rhabdoid cells, with large nuclei containing a single prominent nucleolus, and cytoplasm with distinct pale eosinophilic inclusions. Tumors demonstrating only classic rhabdoid cells are rare, instead, they often have areas composed of spindled or pleomorphic undifferentiated cells without a rhabdoid phenotype. A classic rhabdoid component may be entirely absent. Central nervous system AT/RTs typically demonstrate a variety of primitive neuroectodermal, epithelial or mesenchymal cells, which underlies the difficulty in distinguishing these tumors from other primitive neuroectodermal tumors or choroid plexus carcinomas. Immunohistochemistry is often used in the differential diagnosis, based on the typical expression of smooth muscle actin, epithelial membrane antigen and vimentin. Lack of expression of the SMARCB1 protein is also employed as a specific means of distinguishing rhabdoid tumors from other malignancies with similar histologic features, especially for diagnosis of AT/RT versus primitive neuroectodermal tumors.

Individuals with germline alterations of SMARCB1 are predisposed to rhabdoid tumors of the brain, kidney and soft tissues and may present with more than one primary tumor. These children are most often diagnosed within the first year of life and tend to have a worse prognosis. It is not known whether the poor prognosis is related to the presence of a germline mutation in all of their cells, or the fact that they develop multiple and progressive primary tumors that are resistant to therapy.

The name SMARCB1 (SWI/SNF related, Matrix associated, Actin dependent Regulator of Chromatin, subfamily B, member 1) is derived from its role as a core member of the SWI/SNF chromatin remodeling complex. SMARCB1 is a core subunit present in all variants of the SWI/SNF complex. The protein is highly conserved, as evidenced by an identical amino acid sequence in mice and humans. However, the function of SMARCB1 is poorly understood. There are no SMARCB1 paralogs and the protein lacks particularly informative protein motifs.

The present invention seeks to provide novel therapies for the treatment of cancers such as rhabdoid tumors, as well as methods of selecting an effective treatment regime in cancer patients.

SUMMARY OF THE INVENTION

A first aspect of the invention provides an inhibitor of the ubiquitin-proteasome system for use in treating cancer in a patient, wherein the patient is assessed to establish that the cancer is associated with cells in which functional activity of SMARCB1 is low or absent. The patient is a mammal, in particular a human.

A further aspect of the invention is directed to the use of an inhibitor of the ubiquitin-proteasome system in the preparation of a medicament for treating cancer in a patient wherein the patient is assessed prior to treatment with an inhibitor of the ubiquitin-proteasome system to establish that the cancer is associated with cells in which the functional activity of SMARCB1 is low or absent. Similarly, the invention is directed to a method for selecting a pharmaceutical agent for treating cancer in a patient, the method comprising:

a. determining whether the cancer present in a patient is associated with cells in which the functional activity of SMARCB1 is low or absent; and b. where the cancer is found in step (a) to be associated with cells in which the functional activity of SMARCB1 is low or absent, selecting an inhibitor of the ubiquitin-proteasome system as a pharmaceutical agent for treating cancer in the patient; and optionally c. where the cancer is found in step (a) not to be associated with cells in which the functional activity of SMARCB1 is low or absent, deselecting an inhibitor of the ubiquitin-proteasome system as a pharmaceutical agent for treating cancer in the patient; and/or optionally selecting an anti-cancer agent other than an inhibitor of the ubiquitin-proteasome system as a pharmaceutical agent for treating cancer in the patient.

An interesting aspect relates to a method for identifying a subject as a cancer patient for whom administration of an inhibitor of the ubiquitin-proteasome system would be therapeutically beneficial or identifying a cancer patient for whom administration of an inhibitor of the ubiquitin-proteasome system would be therapeutically beneficial, the method comprising:

d. determining whether the cancer present in a patient is associated with cells in which the functional activity of SMARCB1 is low or absent; and e. where the cancer is found in step (a) to be associated with cells in which the functional activity of SMARCB1 is low or absent, identifying the patient as a cancer patient for whom administration of an inhibitor of the ubiquitin-proteasome system would be therapeutically beneficial; and optionally where the cancer is found in step (a) not to be associated with cells in which the functional activity of SMARCB1 is low or absent, identifying the patient as a cancer patient for whom administration of an inhibitor of the ubiquitin-proteasome system would not be therapeutically beneficial and/or optionally identifying the patient for whom selecting an anti-cancer agent other than an inhibitor of the ubiquitin-proteasome system may be therapeutically beneficial.

Importantly, the invention is directed to a method for treating cancer in a patient, the method comprising:

f. determining whether the cancer present in a patient is associated with cells in which the functional activity of SMARCB1 is low or absent; and g. where the cancer is found in step (a) to be associated with cells in which the functional activity of SMARCB1 is low or absent, administering to the patient an inhibitor of the ubiquitin-proteasome system; and optionally where the cancer is found in step (a) not to be associated with cells in which the functional activity of SMARCB1 is low or absent, not administrating an inhibitor of the ubiquitin-proteasome system; and/or optionally administrating to the patient an anti-cancer agent other than an inhibitor of the ubiquitin-proteasome system.

DESCRIPTION OF THE INVENTION

Figure 1:
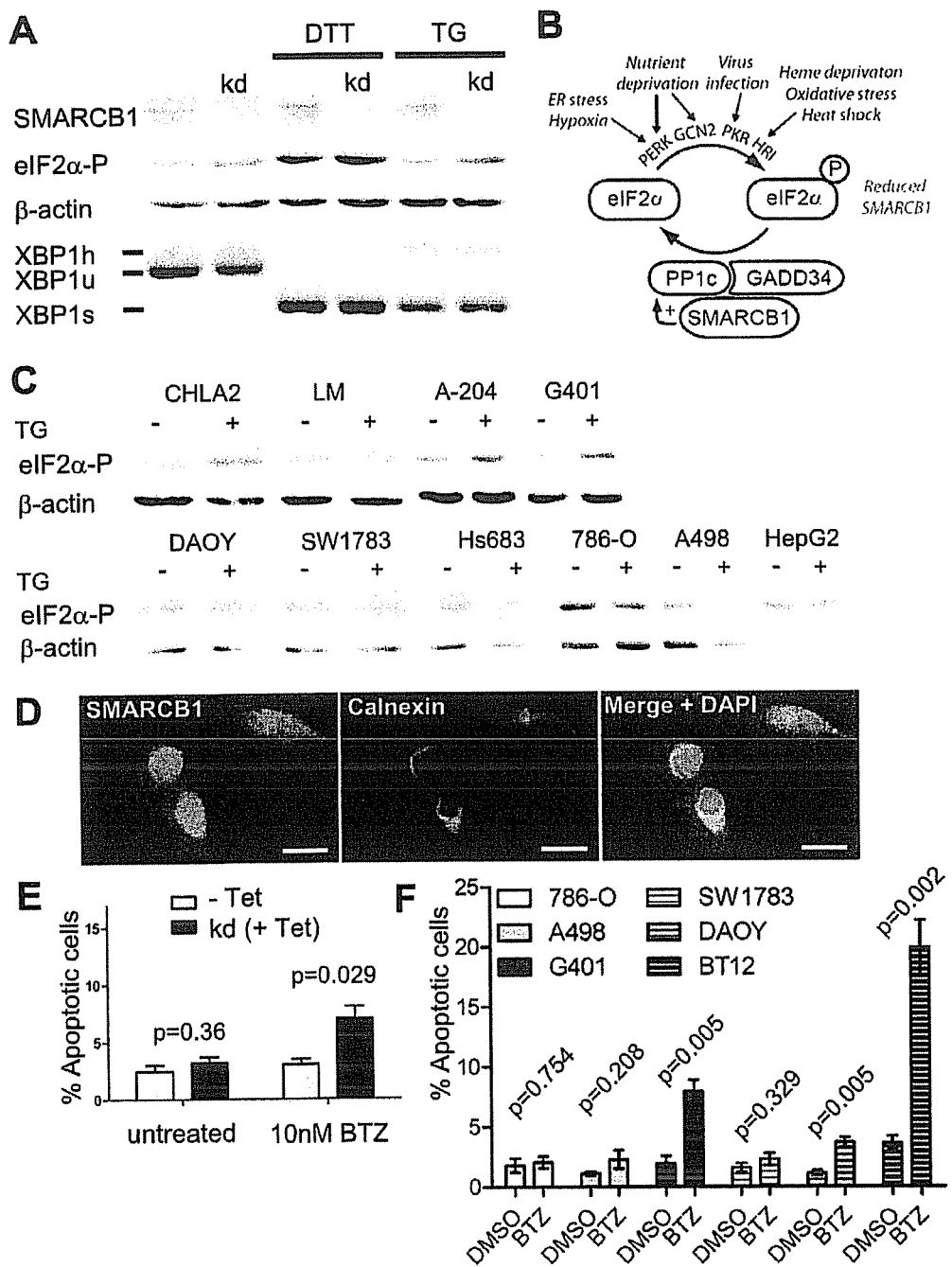
FIG. 1 shows the involvement of SMARCB1 in the unfolded protein response (UPR)

By "inhibitor of the ubiquitin-proteasome system" we mean an agent, such as a small chemical entity, polypeptide or the like, which is capable of inhibiting (at least, in part) a function of the ubiquitin-proteasome system (preferably in vivo in humans). Such an inhibitor may act at any point along the ubiquitin-proteasome protein degradation pathway, for example by inhibiting (at least, in part) the marking of proteins for degradation by modulating ubiquitination or deubiquitination, by inhibiting the ability of the proteasome to recognize or bind proteins to be degraded, and/or by inhibiting the ability of the proteasome to degrade proteins.

The ubiquitin-proteasome system, and components thereof, are described in detail in the scientific literature, for example see Ciechanover, 1998, *The EMBO Journal* 17, 7151-7160 (see FIGS. 1 and 2 therein) and Bedford et al., 2011, *Nat Rev Drug Discov* 10, 29-46.

The inhibitor of the ubiquitin-proteasome system is a proteasome inhibitor acting directly upon the proteasome to inhibit its function. For example, the proteasome inhibitor may inhibit (at least, in part) the ability of the human proteasome to degrade proteins.

Examples of proteasome inhibitors are well known in the art (for example, see de Bettignies & Coux, 2010, *Biochimie.* 92(11):1530-45, Kling et al., 2010, *Nature Biotechnology*, 28(12):1236-1238). Examples include 20S proteasome inhibitor, 26S proteasome inhibitor, hepatitis C virus (HCV) 26S proteasome inhibitor, human immunodeficiency virus (HIV) 26S proteasome inhibitor and proteasome inhibitor.

The inhibitor of the ubiquitin-proteasome system may also be a ubiquitin inhibitor. Examples are well known in the art and include ubiquitin ligase inhibitor, ubiquitin specific peptidase 8 (USP8) inhibitor, ubiquitin-like modifier activating enzyme 3 (UBA3) inhibitor, ubiquitin-specific protease 7 (USP7) inhibitor.

By "SMARCB1" is meant SWI/SNF-related matrix-associated actin-dependent regulator of chromatin subfamily B member 1 protein. The human SMARCB1 protein and mRNA sequences are detailed in Database Accession Nos. Q12824, NP_003064 and NP_001007469.

SMARCB1 is also known in the scientific literature as BAF47, INI1, RDT, RTPS1, SNF5, SNF5L1, Sfh1p, Snr1 and/or hSNFS.

By a cancer "associated with cells" in which the functional activity of SMARCB1 is low or absent, we include that SMARCB1 expression in the cancer cells from the patient is low or absent at the protein and/or mRNA level. Alternatively, the cancer cells may express a mutated form of a SMARCB1 protein having reduced or absent activity (i.e. the mutations lead to loss of function of the SMARCB1 protein).

Thus, in the context of the present the phrase "a cancer found to be associated with cells" in which the functional activity of SMARCB1 is low or absent refers to a cancer comprising cells in which the functional activity of SMARCB1 is likely to be low or absent, or where the functionally activity of SMARCB1 in those cells have been validated to be low or absent. It follows that the cells referred to as being associated with the cancer are cancerous cells, or at least very likely to become cancerous due to the loss of function of the SMARCB1 tumour suppressor.

The patient may have, or is suspected of having, a cancer selected from the group consisting of epithelioid sarcomas, synovial sarcomas, undifferentiated sarcomas without rhabdoid features, extraskeletal myxoid chondrosarcomas, Ewing sarcomas, mucinous carcinomas of the pancreas, malignant peripheral nerve sheath tumours, schwannomas, familial and sporadic schwannomatosis, cribriform neuroepithelial tumours, embryonal central nervous system tumours without rhabdoid features, choroid plexus carcinomas, teratoma, primitive neuroectodermal tumours (PNET), poorly differentiated chordomas, non-hodgkin lymphoma and chronic myeloid leukaemia, meningioma, glioblastoma, myoepithelial carcinoma, collecting duct carcinoma.

For example, the patient may have, or may be suspected of having, breast cancer.

The patient may have, or be suspected of having an atypical teratoid rhabdoid tumour (AT/RT) and/or a malignant rhabdoid tumour (MRT). an undifferentiated sarcoma with rhabdoid features, a renal medullary carcinoma, an embryonal central nervous system tumour with rhabdoid features, A subject is someone not yet diagnosed as having cancer.

The invention provides an inhibitor of the ubiquitin-proteasome system for use in treating a leukemia associated with a translocation of the HRX gene. Leukemic HRX fusion proteins associate with SMARCB1 and inhibit apoptosis induced by the SMARCB1-bound protein GADD34 (Adler et al., *Molecular and Cellular Biology*, 1999, 19(10): 7050-60).

A characteristic feature of the invention is the assessment of the patient to establish that the cancer is associated with cells in which the functional activity of SMARCB1 is low or absent.

By low or absent "functional activity", in this context, we mean reduced or absent expression of SMARCB1 in tumor cells (for example, relative to internal positive controls in tissue samples, such as normal vessel cells, inflammatory cells, surrounding normal tissue or relative to external positive controls) as assessed at the protein and/or mRNA level (for example, Kohashi K et al., Modern Pathology 2010, 23, 981-990), as well as the presence of chromosomal aberrations or DNA mutations (e.g. deletions, missense, nonsense mutations, and the like) or epigenetic alterations (e.g. DNA methylation) that lead to a reduced or lost SMARCB1 activity.

In general, a quantitative or semi-quantitative, standardized control procedure is used to assess the low or absent functional activity of SMARCB1.

Where it is determined that there is no detectable SMARCB1 protein in a cell of a tissue sample, it is reasonable concluded that the functional activity of SMARCB1 is absent or at least low in that cell. The same applies to the scenario where the SMARCB1 mRNA is absent or low compared to a SMARCB1 positive control cell (normal cells). Where the level of SMARCB1 protein is determined to be low compared to a control cell having two (or at least one) fully functional SMARCB1 allele, it may also be concluded the functional activity of SMARCB1 is low in that cell.

Where the SMARCB1 status of the cells are assessed at the DNA level and it is determined that a chromosomal aberration, a DNA mutation (e.g. deletion, missense, nonsense mutation, and the like) or an epigenetic alteration (e.g. DNA methylation) is present in a least one of the SMARCB1 alleles, the DNA aberration/mutation referred to are a chromosomal aberration, or a DNA mutation that affects the functionality of the SMARCB1 allele or the SMARCB1 protein encoded by that allele; for example, a deletion of the entire SMARCB1 allele or parts of the SMARCB1 allele, or the introduction of a mutation in the coding region in such as way that a functional SMARCB1 protein is not expressed from that allele or that the functionality of the SMARCB1 protein encoded by the allele is at least adversely affected. Likewise, the presence of a mutation in an element of the SMARCB1 allele that controls the transcription or splicing of the SMARCB1 mRNA that adversely affects the expression of the SMARCB1 indicates that the affected allele is not functional in the sense that no functional SMARCB1 protein is generated from the affected allele.

The same applies to the scenario where the SMARCB1 allele is determined to be epigenetically modified, e.g. by DNA methylation of one or more CpGs in the SMARCB1 allele, such as one or more CpGs in CpG islands of transcriptional control elements. Epigenetic modifications of genes, such as hypermethylation of genes, are known to be associated with gene silencing. Thus, epigenetic mutations that affect the transcriptional activity of the SMARCB1 allele will manifest itself at the level of SMARCB1 mRNA and thus the protein level in the affected cell. Thus, the low or absent functional activity may manifest itself at the level of the genomic DNA, mRNA, protein and/or activity (i.e. function) of SMARCB1. In general, it is contemplated that the term "low functional activity" should be understood as an activity that is less than 50% of the levels detected in non-cancerous normal cells. A standardized, quantitative or semi-quantitative, control procedure is used to assess the low or absent functional activity of SMARCB1.

It follows that it is not necessary to assess the SMARCB1 protein activity per se. Based on the assessment of the aberration/mutation of the SMARCB1 alleles, it may be concluded that it is likely that no functional activity of the SMARCB1 is present or that the activity is at least significantly reduced if the alleles contains at least one of the above referred to aberrations, mutations or modifications. Likewise, if the SMARCB1 RNA is absent or very low, it may reasonably be concluded that it is likely that the SMARCB1 activity is absent or at least reduced without a further step of assessing the SMARCB1 protein activity per se.

The SMARCB1 status of a cancer patient may be assessed on non-cancerous tissues material, for example a non-cancerous cell sample obtained in the form of a body fluid sample obtained from the patient or a biopsy of tissue that is diagnosed or assumed not to be cancerous.

For prenatal diagnosis, the SMARCB1 status of a patient is assessed on fetal cells, for example trophoblast/chorion villus biopsies, from cells obtained by amniocentesis, from fetal venipuncture, fetoscopy-guided biopsy, or from fetal cells isolated from maternal blood. Another source for prenatal tests is fetal "cell-free" nucleic acids from maternal blood.

Where loss of function is determined for both SMARCB1 alleles, it is likely that no functional or at least no significant SMARCB1 activity is present or that the activity is at least significantly reduced. In that case, is it likely that the cancer patient has a cancer that would benefit from the treatment with an inhibitor of the ubiquitin-proteasome system. The same reasoning applies to the scenario where there is loss-of-function for only one of the alleles, since loss-of-function of function of the second SMARCB1 allele is expected at a later stage of the tumour development (loss of heterozygocity, LOH).

It will be appreciated that the assessment step may be performed at any time before or even during treatment of the patient. Preferably, however, the patient is assessed prior to commencement of treatment with the inhibitor.

The assessment of the patient comprises providing a sample of cells from the patient and measuring the amount of SMARCB1 protein, and/or mRNA encoding the same, in the cells. For example, the assessment of the patient may comprise measuring the amount of SMARCB1 protein in the cells, e.g. by immunohistochemistry, immunofluorescence, Western blot analysis, an immunological assay (e.g., an ELISA or other solid phase-based immunoassay such as SPRIA or amplified ELISA so called IMRAMP), a protein chip assay, surface-enhanced laser desorption/ionization (SELDI), high performance liquid chromatography, mass spectrometry, chemiluminescence, nephelometry/turbometry, lateral flow or pure or polarised fluorescence or electrophoresis.

In a preferred embodiment of the present invention, the SMARCB1 status is assessed at the level of protein by immunohistochemistry on a tissue section of a biopsy obtained from a neoplasm of the patient (benign, potentially malignant (pre-cancer), or malignant (cancer)).

The tissue section is normally prepared by fixing the tissue biopsy (e.g. using paraformaldehyde) and preparing thin slices of tissue (e.g. in the range of 50 nm and 100 μm such as in the range of 3 to 50 μm). If the tissue biopsy is already thin and it is not possible to slice it up, it may be used as whole. The tissue slices may be prepared using a microtome and subsequently mounted on slides.

In order to improve the availability of epitopes on SMARCB1 for antibody binding, an additional step of preparing the fixed tissue section for SMARCB1 antibody staining may be added. The availability of epitopes for antibody binding may be improved by adding a step of deparaffinization and/or antigen retrieval. Antigen retrieval may be accomplished by using microwaves, enzymes or by hot incubation of the tissue section. Further and in order to reduce background staining, a step of blocking or quenching endogenous biotin or enzymes may be performed prior to the application of the SMARCB1 antibody. Unspecific antibody binding may be reduced by the application of isotype matched control antibodies. Alternatively or additionally, blocking buffer may be applied (e.g. serum, non-fat dry milk, BSA or gelatine or commercially available blocking buffers). The surface tension of the tissue section may be reduced (e.g. using Triton X-100, which also increases the epitope accessibility through membrane permeabilization) to reduce the amount of antibody needed for the detection of SMARCB1.

The SMARCB1 antibodies used for specific detection SMARCB1 may be polyclonal or monoclonal. Polyclonal antibodies may be used where it is preferred to detect the SMARCB1 protein by targeting a plurality of epitopes on the SMARCB1 protein. Alternatively, monoclonal antibodies may be applied where the specificity to the SMARCB1 protein is critical, such as in tissues where cross-reactivity of polyclonal SMARCB1 antibodies to other proteins is observed.

The antibodies used for the immunohistochemical detection of SMARCB1 may generally be divided into primary antibodies that are raised against the SMARCB1 protein and secondary antibodies that are raised against immunoglobulins of the primary antibody species.

Where SMARCB1 is detected using only antibodies raised against the SMARCB1 protein (direct one-step detection), the primary SMARCB1 antibody is usually conjugated with means for detecting the primary SMARCB1 antibody, e.g. the conjugation of a linker molecule, such as biotin, that then recruits reporter molecules (e.g. avidin, streptavidin or NeutrAvidin). Alternatively, the primary SMARCB1 antibody may be directly linked to fluorochromes for detection by immunofluorescence or an enzyme, where enzymatic activity is detected using a reporter molecule. Alkaline phosphatase (AP) and horseradish peroxidase (HRP) are extensively used as labels for protein detection. Suitable fluorochromes include but are not limited to FITC, Cy3, APC, rhodamine, APCXL, RPE, BPE, PerCP, Alexa fluorophores such as Alexa 488 and the like.

Where the SMARCB1 protein status is assessed by two-step detection, using a primary antibody against the SMARCB1 protein and secondary antibody against immunoglobulins of the primary antibody, the secondary antibody is preferably conjugated with means for detecting the secondary antibody bound to the primary antibody. The means for detecting the secondary antibody includes the above mentioned for detecting the primary SMARCB1 antibody by the direct (one step) approach. In the two-step approach, the primary SMARCB1 antibody is preferably unlabelled.

Where one of the primary or secondary antibodies is conjugated to an enzyme, the binding of the antibody is detected using a reporter molecule for that enzyme. Suitable reporter molecules include molecules that allows chromogenic and fluorescence detection mediated by interaction with reporter molecules and the enzyme.

In the direct one-step method, the labelled SMARCB1 antibody is contacted directly with the SMARCB1 antigen in tissue sections. While this technique utilizes only one antibody and therefore is simple and rapid, the sensitivity is lower due to little signal amplification, in contrast to the indirect (two step) approach. Therefore the indirect (two-step) is often preferred over the direct one-step method.

In the two-step (indirect) method of detecting the SMARCB1 protein, the detection is preferably accomplished using an unlabeled primary SMARCB1 antibody that binds to the SMARCB1 antigen in the tissue section and a labelled secondary antibody (detection antibody) that reacts with the primary antibody. It follows that the two-step approach is more sensitive than direct detection strategies because of signal amplification due to the binding of several secondary antibodies to each primary antibody if the secondary antibody is conjugated to the fluorescent or enzyme reporter.

In order to identify the discrete cells in the tissue section it may be advantageous to apply a counter strain such as hematoxylin, Hoechst stain or DAPI. The counter staining may also be used to distinguish cells in the tissues section where SMARCB1 protein is absent or significantly reduced. The SMARCB1 protein positive cells in the tissue section may thus serve as positive control for the antibody staining. Alternatively, or in addition, external positive control samples may be used. Such control samples include sections defined as +3 (100% expression), +2 (intermediate high expression), +1 (intermediate low expression), and 0 (no expression).

The immunohistochemical assay used for the detection of SMARCB1 protein should preferably be as simple and rapid as possible. Thus some of the above mentioned steps can be omitted without compromising the sensitivity and specificity of the assay; such steps are preferably not included.

It will be appreciated that the sample of cells from the patient may be cancer cells or may be normal (non-cancerous cells). For example, the latter may be useful for detecting the presence of germline mutations associated with low or absent functional activity of SMARCB1.

Alternatively, or in addition, the assessment of the patient further may comprise measuring the amount of SMARCB1 mRNA, e.g. by quantitative PCR, digital PCR, Northern blot analysis, Next generation sequencing, SAGE, or array technologies.

Alternatively, or in addition, the assessment of the patient further may comprise determining the level of SMARCB1 activity (either directly or indirectly). Such activity may be assayed indirectly, for example by determining the genomic DNA, RNA or cDNA sequence, e.g. by fluorescence in situ hybridization, multiplex ligation-dependent probe amplification, comparative genomic hybridization (CGH), array CGH, other array technologies, or sequencing techniques. Any DNA sequencing method (e.g. methods based on the Sanger method and ABI automated fluorescent sequencers, massively parallel sequencing/high-throughput sequencing/next-generation sequencing technologies) may be used to determine SMARCB1 mutations and genomic alterations (such as deletions).

The sequence information may then be used to identify chromosomal aberrations or DNA mutations that lead to a reduced or lost SMARCB1 activity.

Next generation sequencing methods differ from automated Sanger (first generation) sequencing. They are high-throughput methods that allow the sequencing of large numbers of different DNA sequences in a single reaction (in parallel). The sequential addition of nucleotides to immobilized and spatially arrayed DNA templates is monitored.

The template used in next generation sequencing is double-stranded DNA that may be derived from genomic DNA, cDNA, or immunoprecipitated DNA. Such double-stranded DNA is converted into a library of sequencing reaction templates (sequencing library) by the following steps: fragmentation, size selection, and adapter ligation. A library can be directly sequenced s (single-molecule templates) or is amplified and then sequenced (clonally amplified templates). Template generation also serves to spatially separate and immobilize DNA fragment populations for sequencing, typically by attachment to solid surfaces or beads. This allows the downstream sequencing reaction to operate as millions of microreactions carried out in parallel on each spatially distinct template.

The sequencing is performed by a series of repeating chemical reactions that are carried out and detected automatically. Typically, a flow cell is used which contains the immobilized templates and standardized additions and detections of nucleotides, washing/removal of reagents are performed. Applying such repeated reactions on a nucleotide-by-nucleotide basis allows the sequencing of all DNA templates (the sequencing library) in parallel. Different chemistries are used in different types of next generation sequencing, which include DNA polymerases and DNA ligases.

Data analysis includes several different steps: base calling, sequence alignment/assembly, and final specific analyses.

Since sequencing reactions typically fail to detect copy number changes, the detection of SMARCB1 deletions needs to be done using different techniques, for example PCR-based technologies and hybridization techniques.

The status of the SMARCB1 gene in a tissue sample obtained from the patient may be assessed at the DNA level to detect alterations in the DNA that affect the expression or the functionality of the protein encoded by the mutated SMARCB1 gene. Suitable assays include assays based on PCR-based technologies such as PCR, RT-PCR, DNA sequencing or DNA microarrays, and cytogenetic methods such as karyotyping and fluorescence in situ hybridisation. Common for these assays are the use of SMARCB1 specific probes or primers for SMARCB1 specific application. The probes/primer may be designed for detecting the presence or absence of a SMARCB1 allele or part thereof. Alternatively, the probes are designed for detecting the presence or absence of specific mutations or larger aberrations such as deletions.

One DNA microarray-based method to detect genomic SMARCB1 alterations such as deletions is a SNP array. SNP arrays are used to detect single nucleotide polymorphisms in DNA samples, and genomic SMARCB1 alterations such as deletions can be detected indirectly from SNP array data.

A SNP array can consist of hundreds of thousands of immobilized oligonucleotides (probes) each representing a specific genomic DNA locus and multiple oligonucleotides can represent the same locus. The method is based on the hybridization of labelled single stranded sample DNA to the array in certain buffer solutions. Different types of direct or indirect labelling can be used, for example fluorescent labelling. The method can include washing, blocking, and amplification steps. The amount of labelled sample DNA hybridized to each of the probes on the SNP array is detected and measured as signal intensities. The signal intensity also depends on the affinity between sample and probe DNA. Different bioinformatics tools are used to analyze and interpret the measured signal intensities.

A SMARCB1 deletion (a deletion of one allele) for example results in homozygous genotypes at the SNPs within the deletion. A homozygous SMARCB1 deletion (a deletion of both SMARCB1 alleles) will result in the absence of SNPs (no detection) in this region.

In a basic PCR set up the PCR reaction includes (i) DNA material isolated from the tissue biopsy, (ii) two primers that are complementary to the 3' (three prime) ends of each of the sense and anti-sense strand of the region of the SMARCB1 allele to be analysed, (iii) Taq polymerase or another suitable DNA polymerase with a temperature optimum at around 70° C., (iv) deoxynucleoside triphosphates (dNTPs; nucleotides containing triphosphate groups), (v) a buffer solution, providing a suitable chemical environment for optimum activity and stability of the DNA polymerase (vi) divalent cations, magnesium or manganese ions, (vii) monovalent cation potassium ions.

The basic PCR usually consists of a series of repeated temperature changes, cycles, with each cycle commonly consisting of 2-3 discrete temperature steps, usually three, e.g. initialization step, denaturation step (repeated), annealing step (repeated), elongation step (repeated), final elongation and a final hold step. Variants over the basic PCR technique are numerous, but the majority of the technique includes a series of repeated temperature changes in line with the above.

A variant of the above mentioned basic PCR technology is Reverse Transcription PCR (RT-PCR) using a reverse transcriptase (RT) to reverse transcribes RNA into cDNA, which is then amplified by PCR. RT-PCR is widely used to determine the expression of a gene. RT-PCR may thus be used to assess the level of SMARCB1 transcripts in a tissue sample obtained from the patient. Primers specific for the SMARCB1 transcripts are used to the application and the absence of a product indicates the absence of SMARCB1 expression (or at least the expression of an aberrant transcript), which indicates that the patient carries a cancer likely to belong to the SMARCB1 deficient subtype of cancer likely to be susceptible to the treatment with an inhibitor of the ubiquitin-proteasome system.

Another PCR-based method is multiplex ligation-dependent probe amplification (MLPA). In contrast to FISH, MLPA allows to detect smaller deletions (50-70 bp). As input material, patient DNA isolated from different cell sources is used.

Two MLPA probes (oligonucleotides) for each specific SMARCB1 genomic DNA region are used, and multiple such probes to cover various genomic SMARCB1 regions which are typically part of genomic alterations such as deletions. MLPA probes consist of specific sequences complementary to immediately adjacent genomic SMARCB1 DNA, and primer sequences which are the same for the different probe pairs. After denaturation of the DNA to be tested, MLPA probes bind genomic SMARCB1 regions during a hybridization step. If the two probe oligonucleotides are both hybridized to adjacent SMACRB1 regions, they are ligated during a ligation step and can be amplified in a PCR. The different SMACRB1 sequences are PCR-amplified using one primer pair. Since the probes are designed so that each amplification product has a specific length, a mixture of amplification products results, which can be electrophoresed on a capillary sequencer or on a gel. The relative copy number of each targeted SMARCB1 region is detected based on the peak area or peak height of each amplification product. SMARCB1 deletions and duplications are detected using a control sample as comparison. In case of SMARCB1 deletions, an MLPA probe cannot bind to the respective genomic DNA, resulting in the absence of the ligation and the amplification product.

Another preferred approach to assess the SMARCB1 status is by FISH (fluorescence in situ hybridization). FISH (fluorescence in situ hybridization) is a cytogenetic technique for detecting and localizing the presence or absence of specific DNA sequences on chromosomes. FISH can also be used to detect and localize specific RNA targets tissue sections. In this context, it can help define the spatial-temporal patterns of gene expression within cells and tissues.

In the context of the present invention, FISH may be used to assess the presence or absence of alterations in SMARCB1 alleles of cells obtained from the patient. Preferably, the tissue sample is obtained from neoplastic tissue such as cancer tissue. However, FISH may also be used to assess the status of the SMARCB1 alleles in non-cancerous tissue. The presence of alterations in at least one of the SMARCB1 alleles (deletions, mutations) indicates that the patient carries a cancer likely to belong to the SMARCB1 deficient subtype of cancers susceptible to the treatment with an inhibitor of ubiquitin-proteasome system. Where DNA alteration of the SMARCB1 gene is detected in only one of the alleles that allele is expected to be silent or expressing a non-functional SMARCB1 protein. Detecting a heterozygous DNA alteration of SMARCB1 gene in non-cancerous tissue indicates that the alteration is an early event (e.g. a germline mutation) and that the other SMARCB1 allele is likely to be deficient in the cancer tissue (loss of heterozygocity). In the cancer tissue, the other SMARCB1 allele may be deficient due to another alteration of the allele (for example other mutations, deletions or epigenetic mutations such as DNA methylation).

The tissue sections for the in situ hybridization are prepared much in line with the preparations of tissue sections for immunohistochemistry detections as described herein. Tissue sections may be prepared as frozen section, which is generally done by rapidly freezing the tissue biopsy (e.g in a −80 freezer) and then when frozen embedded in a special support medium for thin cryosectioning. The sections are lightly and rapidly fixed in 4% paraformaldehyde just prior to processing for hybridization. Alternatively, the tissue biopsy is fixed in formalin as one would normally fix tissues for histology and then embedded in wax (paraffin sections) before preparing the tissue sections. The tissue section is typically subject to a further step of permeabilization to make the cells and the DNA accessible to probes for detections of the SMARCB1 gene. Reagents often used to permeabilize tissue are HCl, detergents (Triton or SDS) and Proteinase K.

The probes used for detecting DNA alteration of the SMARCB1 gene (or detecting SMARCB1 mRNA) are typically in the range of 20 to 40 base pairs, but may be up to 1000 base pairs. Generally, four types of probes are used for FISH: oligonucleotide probes, single stranded DNA probes, double stranded DNA probes and RNA probes. A control probe is preferably included as control for the quality and the efficacy of the assay.

Oligonucleotide probes are generally small around 40-50 base-pairs, which allows easy penetration into the cells of the tissue sections and thus optimal for in situ hybridization. Further, such probes may be made resistant to RNase degradation. The oligonucleotide probes are designed to detect specific mutations and deletions of the SMARCB1 gene. In addition, because they are synthetically designed, it is possible to make a series of probes that have the same GC content; Since G/C base pairs bond more strongly than A/U base pairs, differences in GC content would require different hybridization conditions, so with oligonucleotides protocols can be standardized for many different probes irrespective of the target genes being measured.

Single stranded DNA probes (ssDNA) may be used to scan a larger region of the SMARCB1 gene for alterations such as deletions since ssDNA probes are generally larger (e.g. in the range of 200-500 bp size). Single stranded DNA probes are typically prepared by reverse transcription of RNA or by amplified primer extension of a PCR-generated fragment in the presence of a single antisense primer.

Double stranded DNA probes (dsDNA), like single ssDNA probes, are generally large (e.g. in the range of 200-500 bp size), but are easier and cheaper to prepare. Double stranded DNA probes are generally less sensitive because of the tendency of the DNA strands to rehybridize to each other and are preferably not used.

RNA probes have the advantage that RNA-RNA hybrids are very thermostable and are resistant to digestion by RNases. This allows the possibility of post-hybridization digestion with RNase to remove non-hybridized RNA and therefore reduces the possibility of background staining.

In order to detect hybridization to the SMARCB1 gene, the probes are usually 5' or 3' end-labeled or 3' tailed with modified nucleotides that have a label attached (detection means) that can be detected after the probe has hybridized to the SMARCB1 gene or the locus comprising the SMARCB1 gene. With end-labeling a single modified ddNTP (that incorporates the label) is added to either the 5' or the 3' end of the molecule enzymatically or during probe synthesis. 3' tailing involves addition of a tail (on average 5-50 nucleotides long of modified dNTPs depending on the method used) using the enzyme terminal transferase (TdT). The label (detection means) may biotin or a fluorochrome (e.g. FITC, Cy3, APC, rhodamine, APCXL, RPE, BPE, PerCP, Alexa fluorophores such as Alexa 488 or the like).

The probes are typically applied in the form of a hybridization solution. Hybridization depends on the ability of the oligonucleotide to anneal to a complementary mRNA strand just below its melting point (Tm) and the temperature during the hybridization is adjusted accordingly. Following hybridization the material is washed to remove unbound probe or probe which has loosely bound to imperfectly matched sequences. Washing should be carried out at or close to the stringency condition at which the hybridization takes place with a final low stringency wash. Hybrization to the SMARCB1 gene is detected using means suitable for FISH and capable of detection the label applied in the assay. The absence of hybridization of the SMARCB1 specific probe to a SMARCB1 allele indicates that the SMARCB1 allele is deficient.

The FISH assay for detection of DNA alterations the SMARCB1 gene may be applied to cancerous tissues as well as non-cancerous tissue obtained from the subject (patient). Preferably, FISH assay is applied for detection of DNA alterations in the SMARCB1 gene in a subject having or suspected to have a cancer such as a cancer described herein. Where a DNA alteration is detected in both SMARCB1 alleles gene, silencing of both alleles (or expression of non-functional proteins) are expected and the patient is likely to have a cancer belonging to the SMARCB1 deficient subtype of cancers susceptible to the treatment with an inhibitor of ubiquitin-proteasome system. Where a DNA alteration is detected in only one of the SMARCB1 alleles (heterozygous, e.g. due to an early event) that allele is expected to be silent (or expressing a non-functional protein). In that case, the patient carries a cancer, which is also likely to belong to the SMARCB1 deficient subtype of cancer susceptible to the treatment with an inhibitor of ubiquitin-proteasome system, since the second allele of the SMARCB1 gene is also likely to be deficient due to a later event (loss of heterozygocity), e.g. hypermethylation, deletion, mutation.

Alternatively, or in addition, the assessment of the patient further may comprise determining epigenetic alterations (e.g. DNA methylation, histone modifications), that lead to low or absent SMARCB1 gene expression e.g. by DNA methylation analyses, chromatin immunoprecipitation-based techniques, mass spectrometry, chemical reactions (e.g. bisulfite treatment).

Thus, the absence of the SMARCB1 protein may be associated with the epigenetic silencing of one or both of the SMARCB1 alleles due to DNA hypermethylation. The DNA hypermethylation of one of the SMARCB1 alleles may be an early event in the tumour development and the hypermethylated SMARCB1 alleles may even be present in the germline of the subject. Hypermethylation of one or both of the SMARCB1 alleles may also be a late event in the tumour progression.

DNA methylation can be detected in a variety of different ways, most of which is based on a chemical reaction of sodium bisulfite with DNA that converts unmethylated cytosines of CpG dinucleotides to uracil (UpG). Methylated cytosines will not be converted in this process, and primers are designed to overlap the CpG site of interest, which allows one to determine methylation status as methylated or unmethylated. The sodium bisulfite treatment of the DNA extracted from the tissue sample is usually followed by a step of amplification (e.g. by PCR) of SMARCB1 specific primers or hybridization with a SMARCB1 specific probe.

In Methylation-Specific PCR (MSP) the sodium bisulfite treatment of DNA extracted from the tissue sample is followed by PCR. In whole genome bisulfite sequencing (BS-Seq), the sodium bisulfite conversion of genomic DNA is sequenced on a Next-generation sequencing platform. The sequences obtained are then re-aligned to the reference genome to determine methylation states of CpG dinucleotides based on mismatches resulting from the conversion of unmethylated cytosines into uracil.

Detection of DNA methylation by pyrosequencing is also performed on bisulfite treated DNA. This is sequencing of an amplicon made by a normal forward primer but a labelled (e.g. biotinylated) reverse primer to PCR the gene of choice, i.e. the SMARCB1 gene. The sample is analysed on Pyrosequencer by denaturing the DNA and adding one nucleotide at a time to the mix according to a sequence given by the user. If there is a mis-match, it is recorded and the percentage of DNA for which the mis-match is present is noted. The percentage of DNA for which the mis-match is present is noted is used to calculate the percentage of methylation per CpG island.

Another common method to detect DNA methylation makes use of isolating methylated DNA fragments via an antibody raised against 5-methylcytosine (5mC): Methylated DNA immunoprecipitation (MeDIP or mDIP). MeDIP can be combined with PCR using SMARCB1-specific primers, microarray hybridizations (MeDIP-chip) or Next generation sequencing (MeDIP-seq).

The application of any of the above assays for the detection of DNA hypermethylation of one or both of the SMARCB1 alleles implies the use of SMARCB1 specific oligonucleotides designed to detect the methylation of CpG dinucleotides in CpG SMARCB1, such as in the promoter region of the SMARCB1.

The DNA hypermethylation assay for detection of DNA hypermethylation the SMARCB1 gene may be applied to cancerous tissues as well as non-cancerous tissue obtained from the subject (patient). Preferably, DNA hypermethylation assay is applied for detection of DNA hypermethylation in a patient having or suspected to have a cancer such as described herein. Where DNA hypermethylation is detected in both SMARCB1 alleles gene silencing of both alleles are expected and the cancer the patient carries is likely to belong to the SMARCB1 deficient subtype of cancer susceptible to the treatment with an inhibitor of ubiquitin-proteasome system. Where DNA hypermethylation is detected in only one of the SMARCB1 alleles (heterozygous, e.g. due to an early event) that allele is expected to be silent. In that case, the patient carries a cancer, which is also likely to belong to the SMARCB1 deficient subtype of cancers susceptible to the treatment with an inhibitor of ubiquitin-proteasome system, since the second allele of the SMARCB1 gene is also likely to be deficient due to a later event (e.g. hypermethylation, deletion, mutation).

eIF2alpha phosphorylation and/or PP1 activity can be used as indirect markers of SMARCB1 activity.

However, it would be apparent to a person skilled in the art that this list of techniques is not complete and these techniques are not the only suitable methods which may be used in the present invention for measuring the functional activity (e.g. expression) of SMARCB1.

The assessment may further comprise measuring the amount of SMARCB1 protein, mRNA encoding the same and/or other measure of functional activity (sequence) in one or more control samples of cells. Such control samples may include negative control samples (in which SMARCB1 functional activity is known to be low or absent) and/or positive control samples (in which SMARCB1 functional activity is known to be at substantial levels).

Thus, the assessment may comprise performing a biopsy to extract a sample of cancer cells from the patient, which cells can then be tested (either directly or indirectly as a primary cell culture) to determine the functional activity (e.g. expression) of SMARCB1 therein.

Alternatively, or in addition, normal tissue or cells from the patient may be used to determine the functional activity (e.g. expression) of SMARCB1 therein as germline mutations have been found in patients with familial or sporadic tumours (see for example Sevenet et al., 1999, *Am J Human Genet.* 65, 1342-8; Eaton et al., 2011; *Pediatr Blood Cancer* 56, 7-15).

However, persons of skill in the art will appreciate that the functional activity (e.g. expression) of SMARCB1 may be determined indirectly.

Thus, the assessment of the patient may comprise diagnosing the type of cancer from which the patient is suffering (using conventional methods well known in the art for cancer diagnosis). This diagnosis can then be used to determine the functional activity (e.g. expression) of SMARCB1 in the cancer cells (either through the empirical knowledge of the physician or by consulting a database of gene expression and gene function in known cancer types (such as Gene expression omnibus, ArrayExpress, SAGEmap, Ref ExA, caArrayData Portal, GeneX, HuGEIndex, TOGA databases, RCGDB, International Cancer Genome Consortium databases, Mitelman database of Chromosome Aberrations and Gene Fusions in Cancer, SKY/M-FISH&CGH database, COSMIC, TmaDB, YMD, dbEST, TMAD, GXA, SMD, Novartis Gene Expression Database, OncoMine and similar databases). Upon determining that the cancer from which the patient is suffering is associated with (cancer) cells in which the function activity (e.g. expression) of SMARCB1 is low or absent, the patient may be administered an inhibitor of the ubiquitin-proteasome system as a therapeutic agent to treat the cancer.

The inhibitor of the ubiquitin-proteasome system may be an inhibitor selected from the table below.

| Name of product (Other names) | Stated indication | Active ingredient | Route of administration | Dev. phase | Product description |
|---|---|---|---|---|---|
| CEP28331 | Multiple Myeloma | Not Available | Oral | Pre-clinical | Proteasome inhibitor - CEP-28331 is a proteasome inhibitor that blocks the action of proteasomes, cellular complexes that break down proteins, like the p53 protein. CEP-28331 is being developed as an oral formulation for the treatment of multiple myeloma. |
| ONX0914 (immuno-proteasome inhibitor, ONX 0914, PR 957, PR957) | Autoimmune Diseases | Not Available | Not available | Pre-clinical | Proteasome inhibitor - ONX-0914 is an immuno proteasome selective inhibitor which targets proteasome function and block the production of key inflammatory mediators such as Tumor Necrosis Factor-alpha (TNF-alpha) and Interleukin-6 (IL-6). ONX-0914 is being developed for the treatment of autoimmune disorders, such as rheumatoid arthritis, inflammatory bowel disease and lupus. |
| Proteasome Inhibitor | Cancer | Not Available | Oral | Pre-clinical | Proteasome Inhibitor, a small molecule inhibitor of ubiquitin-proteasome system (UPS) is an orally active, non-peptide, non-boron based candidate leading to the inhibition of proteasome activity. The proteasome is an important cellular structure necessary for the growth and function of cancer cells and inhibition of the proteasome has been shown to promote cell cycle arrest and cancer cell death or apoptosis. Proteasome Inhibitor is being developed using TRAP technology for the treatment of cancer. |
| VL01 | Hepatitis C | Not Available | Not available | Pre-clinical | VL01 is a proteasome inhibitor which inhibits HCV replication by inhibiting specific cellular structures, such as the 26S proteasome, and therefore preventing the virus from developing resistance. VL01 is being developed for the treatment of HCV infections. |
| E18770 | Cancer | Not Available | Intravenous; Oral | Phase I | Proteasome inhibitor - E-18770 is an orally active and reversible P2 threonine boronic acid inhibitor of the chymotrypsin activity of mammalian proteasome. It acts by inhibiting nuclear factor-kappaB (NF-kB) activation and IkB degradation and induces the apoptosis in cancer cells. E-18770 is being developed as an intravenous formulation for the treatment of solid tumors or non-Hodgkin's lymphoma, mantle cell lymphoma, bone metastases and multiple myeloma. |
| MLN9708 (MLN2238) | Hematological Malignancies | ixazomib citrate | Intravenous; Oral | Phase I | Proteasome inhibitor - MLN9708 contains ixazomib citrate, second generation proteasome inhibitor as an active ingredient. Ixazomib blocks the action of proteasome, cellular complexes that break down proteins, like the p53 protein. MLN9708 is being developed as an intravenous and oral formulation for the treatment of hematological malignancies, advanced non-hematologic malignancies, solid tumors, multiple myeloma and relapsed or refractory light-chain amyloidosis. |

-continued

| Name of product (Other names) | Stated indication | Active ingredient | Route of administration | Dev. phase | Product description |
|---|---|---|---|---|---|
| NPI0052 (Salino-sporamide A) | Lymphoma | marizomib | Not available | Phase I | Proteasome inhibitor - NPI-0052 contains marizomib (salinosporamide A), a proteasome inhibitor derived from a novel marine-obligate actinomycete. It acts by inhibiting proteasome activity thereby preventing the TNF-alpha induced activation of NF-kappa B. In addition, this proteasomal inhibition results in the accumulation of the Cdk inhibitors, p21 and p27, which sensitize cells to apoptosis. NPI-0052 is being developed for the treatment of multiple myeloma and lymphomas. |
| CEP18770 (CT18770, E 18770, E/CEP 18770, NP47098) | Multiple Myeloma | Not Available | Intravenous; Oral | Phase II | Proteasome inhibitor -CEP-18770 is a reversible P2 threonine boronic acid inhibitor of the chymotrypsin activity of mammalian proteasome. It acts by inhibiting nuclear factor-kappaB (NF-kB) activation and IkB degradation and induces the apoptosis in cancer cells. CEP-18770 is being developed in phase II as oral and intravenous formulation for the treatment of multiple myeloma. CEP-18770 was previously under development as an oral and intravenous formulation for the treatment of solid tumors or non-Hodgkin's lymphoma, mantle cell lymphoma, bone metastases and multiple myeloma. |
| ONX0912 (PR047, oral proteasome inhibitor) | Hematological Malignancies | Not Available | Not available | Phase II | ONX0912 is an oral 20S proteasome inhibitor and an analog of PR-171 which offers greater flexibility in dosing schedule and achieves prolonged proteasome inhibition that may increase efficacy. ONX0912 is being developed as oral formulation for the treatment of hematological malignancies. <br>This product is added upon the acquisition of Proteolix, Inc. |
| PR171 | Solid Tumors | carfilzomib | Intravenous | Phase II | Proteasome inhibitor - PR171 contains carfilzomib, a synthetic analog of epoxomicin. It is a novel proteasome inhibitor that has high selectivity for the N-terminal threonine active sites within the proteasome. PR171 is being developed using CyDex Captisol technology as intravenous formulation for the treatment of relapsed and refractory multiple myeloma, advanced solid tumors and Non-Hodgkin's Lymphoma. |
| Velcade (C68 22, LBH589, LDP 341, MLN 341, PS 341, LDP341, MG 341, MLN341, PS341, SB1, Sch60936, TNK tPA) | Multiple Myeloma | bortezomib | Intravenous; Oral; Subcutaneous | Marketed | Velcade contains bortezomib which is a proteasome inhibitor. Proteasomes are enzyme complexes which are present in all cells which break down intracellular proteins in a regulated manner in both healthy and cancerous cells. Inhibition of the proteasome by Velcade prevents the regulated breakdown of these intracellular proteins, thereby interfering with many of these varied functions. This disruption of |

-continued

| Name of product (Other names) | Stated indication | Active ingredient | Route of administration | Dev. phase | Product description |
|---|---|---|---|---|---|
| | | | | | essential pathways in cancer cells can lead to cell death and inhibit tumor growth. Velcade is indicated for the treatment of patients with multiple myeloma and for the treatment of patients with mantle cell lymphoma who has received at least one prior therapy. It is also being developed for the treatment of solid tumors, B-cell Lymphoproliferative disorder, chronic graft versus host disease and relapsed/refractory T-cell prolymphocytic leukemia. Past identified but halted indications include Chronic Lymphocytic Leukemia, Bronchioloalveolar Carcinoma, Non-Small-Cell Lung Cancer and Amyloidosis. |
| HCV Proteasome Inhibitor | Hepatitis C | Not Available | Not available | Not available | HCV proteasome inhibitor inhibits HCV replication by inhibiting specific cellular structures, such as the 26S proteasome, and therefore preventing the virus from developing resistance. HCV protease inhibitor is being developed for the treatment of HCV infections. |
| HIV Proteasome Inhibitor | AIDS/HIV | Not Available | Not available | Not available | Proteasome inhibitor - HIV Protease Inhibitor inhibits specific cellular targets essential for HIV replication, such as the 26S proteasome, and preventing the virus from developing resistance to this class of drugs by undergoing rapid mutations. HIV proteasome inhibitor is being developed for the treatment of HIV infections. |
| KRX0401 (266, D21266, KRX0401, NSC639966) | Multiple Myeloma | perifosine | Intravenous; Oral | Not available | Proteasome inhibitor - KRX-0401 contains perifosine, an alkyl phosphocholine with structural similarity to phospholipids that are main constituents of cellular membranes. It is a novel, potentially first-in-class, oral anti-cancer agent that modulates Akt, a protein in the body associated with tumor survival and growth. It also modulates a number of other key signal transduction pathways, including the JNK and MAPK pathways, which are pathways associated with programmed cell death, cell growth, cell differentiation and cell survival. KRX-0401 is being developed for the treatment of relapsed or refractory multiple myeloma. |
| Proteasome inhibitor | Cancer | Not Available | Not available | Not available | Proteasome inhibitor is being developed for the treatment of cancer. |
| Imuno-proteasome Specific Inhibitor | Hematological Malignancies | Not Available | Not available | Discontinued | Proteasome inhibitor - Immunoproteasome specific inhibitor is acts by inhibiting the immunoproteasome which is a unique form of the proteasome in this three catalytic subunits are different from those of the standard proteasome. It does not cross-react with the constitutive proteasome and it has cytotoxic activity against hematologic tumor cell lines. Immunoproteasome specific inhibitor is being |

-continued

| Name of product (Other names) | Stated indication | Active ingredient | Route of administration | Dev. phase | Product description |
|---|---|---|---|---|---|
| | | | | | developed for the treatment of hematological cancers. This product was added to Onyx upon the acquisition of Proteolix, Inc. |
| MLN273 | Inflammation | Not Available | Not available | Discontinued | MLN-273 is a novel small molecule proteasome inhibitor. MLN-273 was under development for the treatment of inflammation. |
| MLN519 (LDP-519) | Cerebral Ischemia | Not Available | Parenteral | Discontinued | MLN-519 (formerly known as LDP-519) is a small molecule drug candidate that acts through the inhibition of the proteasome. It is designed to act on a key intracellular mechanism that controls the activation of inflammatory molecules. MLN-519 was under the development as parenteral formulation for the treatment of cerebral ischemia. |
| Tetra-acridines | Cancer | Not Available | Not available | Discontinued | Tetra-acridines are dual inhibitors of topoisomerase II and proteasome that act by blocking the tumor growth. Tetra-acridines were under development for the treatment of cancer. |
| MLN4924 | Hematological Malignancies | Not Available | Intravenous | Phase I | Ubiquitin inhibitor - MLN4924 is a new small molecule which acts as inhibitor of NEDD8 (neural precursor cell expressed developmentally down-regulated 8) activating enzyme (NAE). NAE controls a subset of proteins in the ubiquitin proteasome pathway (UPP) that regulate cancer cell survival. MLN4924 is being developed as intravenous formulation for the treatment of multiple myeloma, hematological malignancies and solid tumors. |
| HBX19818 | Chronic Lymphocytic Leukemia | Not Available | Not available | Not available | Ubiquitin inhibitor - HBX19818 is a specific inhibitor of ubiquitin specific protease 7 (USP7), which may sensitise tumours with ATM and TP53 defects. HBX19818 is being developed for the treatment of chronic lymphocytic leukemia (CLL). |
| HBX41108 (USP7 Inhibitors) | Cancer | Not Available | Not available | Not available | Ubiquitin inhibitor - HBX41108 is an ubiquitin-specific protease 7 (USP7) inhibitor that acts by blocking USP7. This results in the activation of functional p53 and in the growth inhibition of p53-dependent cancer cells. HBX41108 is being developed for the treatment of cancer. |
| Ubiquitin Ligase Inhibitors | Cancer | Not Available | Not available | Not available | Ubiquitin inhibitor - Ubiquitin ligase inhibitors are novel and regulate mitosis or cell division to stop growth and induce apoptosis in cancer cell. Ubiquitin ligases are enzymes involved in many important cellular functions, including cell division and the progression of certain cancers. Ubiquitin ligase inhibitors are being developed for the treatment of cancer. |
| USP8 Inhibitors | Cancer | Not Available | Not available | Not available | Ubiquitin inhibitor - USP8 Inhibitors inhibit ubiquitin-specific proteases 8 (USP8), belonging to a family of cysteine-proteases implicated in the regulation of protein degradation. It removes |

| Name of product (Other names) | Stated indication | Active ingredient | Route of administration | Dev. phase | Product description |
|---|---|---|---|---|---|
| | | | | | ubiquitin from specific protein substrates that allows protein salvage from proteasome degradation, regulation of protein localization or activation. USP8 Inhibitors are being developed for the treatment of cancer. |
| CC12507 | Cancer | Not Available | Not available | Discontinued | Ubiquitin inhibitor - CC12507 is an ubiquitin ligase modulator which regulates a broad range of cellular processes including cell proliferation, differentiation and survival or death. It also modulates key cell signaling proteins. CC12507 was under development for the treatment of cancer but was likely discontinued in the early 2000's. |
| HBX99200 | Cancer | Not Available | Not available | Discontinued | Ubiquitin inhibitor - HBX 99,200 is an inhibitor of ubiquitin-specific proteases 8 (USP8), belonging to a family of cysteine-proteases implicated in the regulation of protein degradation. It removes ubiquitin from specific protein substrates that allows protein salvage from proteasome degradation, regulation of protein localization or activation. HBX 99,200 is being developed for the treatment of cancer. |
| P5091 (P005091) | Multiple Myeloma | Not Available | Not available | Pre-clinical | Ubiquitin ligase inhibitor - P5091 is an USP7 inhibitor which is being developed using DUB technology platform for the treatment of multiple myeloma. |

More specifically, the inhibitor of the ubiquitin-proteasome system may be a proteasome inhibitor selected from the group consisting of bortezomib (PS-341, MG-341, Velcade®), PI-083, MLN 9708, MLN 4924, MLN 519, carfilzomib, ONX 0912, CEP-1877, NPI-0047, NPI-0052, BU-32 (NSC D750499-S), PR-171, IPSI-001, and natural products with proteasome-inhibitory effects, such as green tea polyphenol (−)-epigallocatechin-3-gallate (EGCG), soy isoflavone genistein, and the spice turmeric compound curcumin.

For example, the proteasome inhibitor may be bortezomib (Proprietary name=Velcade®, IUPAC name=[(1R)-3-methyl-1-({(2S)-3-phenyl-2-[(pyrazin-2-ylcarbonyl)-amino]propanoyl}amino)butyl]boronic acid, CAS number=179324-69-7). In another embodiment, the proteasome inhibitor is Carfilzomib (Kyprolis).

The inhibitor may also be a proteasome or a ubiquitin inhibitor selected from the table.

It will be further appreciated by persons skilled in the art that the inhibitor of the ubiquitin-proteasome system may be formulated at various concentrations, depending on a number of factors including the efficacy/toxicity of the inhibitor being used and the indication for which it is being used. Of course, the maximum concentration in any given pharmaceutical formulation will be limited by the maximum solubility of the inhibitor therein. However, the formulations should contain an amount of the inhibitor sufficient to provide an in vivo concentration at or near the target cancer cells which is sufficient to induce their cell death (e.g. via apoptosis). The concentration or amount necessary to provide the desired effect depends on the potency of the inhibitor in question and can be established by methods known by a person skilled in the art or be already available information. The same applies to the daily dose and the dosage regime for the individual inhibitors.

In general, the inhibitor of the ubiquitin-proteasome system is formulated at a concentration of between 1 nM and 1 M. For example, the pharmaceutical formulation may comprise a proteasome inhibitor at a concentration of between 1 µM and 1 mM, for example between 1 µM and 100 µM, between 5 µM and 50 µM, between 10 µM and 50 µM, between 20 µM and 40 µM or about 30 µM.

The inhibitors of the ubiquitin-proteasome system will generally be administered in admixture with a suitable pharmaceutical excipient, diluent or carrier selected with regard to the intended route of administration and standard pharmaceutical practice (for example, see Remington: The Science and Practice of Pharmacy, 19$^{th}$ edition, 1995, Ed. Alfonso Gennaro, Mack Publishing Company, Pennsylvania, USA; incorporated herein by reference). Suitable routes of administration are discussed below, and include intravenous, oral, pulmonary, intranasal, topical, aural, ocular, bladder and CNS delivery.

For example, the inhibitor of the ubiquitin-proteasome system may be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The formulations may alternatively be administered parenterally, for example, intravenously, intraarterially, intratumorally, peritumorally, intraperitoneally, intrathecally, intraventricularly, intrasternally, intracranially, intra-muscularly or subcutaneously (including via an array of fine needles or using needle-free Powderject® technology), or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The inhibitors of the ubiquitin-proteasome system may also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetra-fluoroethane, a hydrofluoroalkane such as 1,1,1,2-tetrafluoroethane (HFA 134A$^3$ or 1,1,1,2,3,3,3-heptafluoropropane (HFA 227EA$^3$), carbon dioxide or other suitable gas. In the case of a pressurised aerosol, the dosage unit may be determined by providing a valve to deliver a metered amount. The pressurised container, pump, spray or nebuliser may contain a solution or suspension of the active proteasome inhibitor, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound for delivery to the patient. It will be appreciated that the overall dose with an aerosol will vary from patient to patient and from indication to indication, and may be administered in a single dose or, more usually, in divided doses throughout the day.

Alternatively, other conventional administration routes known in the art may also be employed; for example the formulation of the invention may be delivered orally, buccally or sublingually in the form of tablets, capsules, ovules, elixirs, solutions or suspensions, which may contain flavouring or colouring agents, for immediate-, delayed- or controlled-release applications. The formulation may also be administered intra-ocularly, intra-aurally or via intracavernosal injection (see below).

For application topically, e.g. to the skin, the inhibitor of the ubiquitin-proteasome system can be administered in the form of a lotion, solution, cream, gel, ointment or dusting powder (for example, see *Remington*, supra, pages 1586 to 1597). Thus, the proteasome inhibitors can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, e-lauryl sulphate, an alcohol (e.g. ethanol, cetearyl alcohol, 2-octyldodecanol, benzyl alcohol) and water.

Formulations suitable for topical administration in the mouth further include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The formulation may also be administered by the ocular route, particularly for treating diseases of the eye. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For veterinary use, a compound is administered as a suitably acceptable formulation in accordance with normal veterinary practice and the veterinary surgeon will determine the dosing regimen and route of administration which will be most appropriate for a particular animal.

In one particular embodiment, the formulation is suitable for systemic administration to a patient (for example, via an oral or parenteral administration route).

The formulation comprising the inhibitor of the ubiquitin-proteasome system may be stored in any suitable container or vessel known in the art. It will be appreciated by persons skilled in the art that the container or vessel should preferably be airtight and/or sterilised. Advantageously, the container or vessel is made of a plastics material, such as polyethylene.

The inhibitor of the ubiquitin-proteasome system will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

The inhibitor of the ubiquitin-proteasome system is administered at a dose sufficient to induce cell death (e.g. apoptosis) of cancer cells in the patient being treated. Thus, the dose of the proteasome inhibitor may be chosen in order to inhibit the growth and/or number of cancer cells in the patient.

It will be appreciated that the dose of inhibitor of the ubiquitin-proteasome system may be changed during the course of treatment of the patient. For example, a higher dose may be used during an initial therapeutic treatment phase of an existing cancer, followed by a lower 'maintenance' dose after the initial treatment is complete to prevent recurrence of the cancer.

The inhibitor of the ubiquitin-proteasome system (e.g. a proteasome inhibitor such as bortezomib) is normally administered at a dose of between 0.5 to 100 mg/m$^2$ per dose such as between 0.5 to 1.3 mg/m$^2$ per dose, which may be repeated at regular intervals (for example daily, twice weekly, weekly, bi-weekly, monthly, etc).

It will be appreciated by persons skilled in the art that the inhibitor of the ubiquitin-proteasome system may be for use as a sole treatment for cancer in a patient or as part of a combination treatment (which further treatment may be a pharmaceutical agent, radiotherapy and/or surgery).

Thus, the patient may also receive one or more further treatments for cancer, for example pharmaceutical agents (such as chemotherapeutic agents), radiotherapy and/or surgery.

The one or more further treatments are selected from the group consisting of conventional chemotherapeutic agents (such as alkylating agents, anti-metabolites, plant alkaloids and terpenoids, topoisomerase inhibitors and antineoplastics), radiotherapeutic agents, antibody-based therapeutic agents (such as gemtuzumab, alemtuzumab, rituximab, trastuzumab, nimotuzumab, cetuximab, bevacizumab), and steroids.

The invention also provide the use of an inhibitor of the ubiquitin-proteasome system in the preparation of a medicament for treating cancer in a patient, wherein the patient is assessed prior to treatment with the inhibitor to establish that the cancer is associated with cells in which the functional activity (e.g. expression) of SMARCB1 is low or absent.

Preferred features of this and further aspects of the invention are described above in relation to the proteasome inhibitors of the invention.

The invention provides:
(a) a method for selecting a pharmaceutical agent for treating cancer in a patient, the method comprising:
  (i) determining whether the cancer present in a patient is associated with cells in which the functional activity (e.g. expression) of SMARCB1 is low or absent or likely to be low or absent; and
  (ii) where the cancer is found in step (a) to be associated with cells in which the functional activity (e.g. expression) of SMARCB1 is low or absent or likely to be low or absent, selecting an inhibitor of the ubiquitin-proteasome system as a pharmaceutical agent for treating cancer in the patient.

Step (i) comprises (a) obtaining a biological sample from a patient, (b) in vitro measuring the functional activity of SMARCB1 in the sample, and (c) comparing the activity found to a threshold value. The threshold value is e.g. determined from biological samples from subjects with normal functional activity of SMARCB1. The biological patient sample could be, for example, from biopsies of the primary tumour, local or distant metastases, or cancer cells in body fluids (e.g. blood, cell aspirates, urine, cerebrospinal fluid).

Step ii) comprises selecting an inhibitor as described herein.

Whenever relevant, the above description of step (i) and (ii) is also valid for other aspects of the invention, i.e. this is also relevant for the following (b), (c) and (d).
(b) a method for identifying a cancer patient or a subpopulation of cancer patients for whom administration of an inhibitor of the ubiquitin-proteasome system would be therapeutically beneficial, the method comprising:
  (i) determining whether the cancer present in a patient is associated with cells in which the functional activity (e.g. expression) of SMARCB1 is low or absent or at least likely to be low or absent; and
  (ii) where the cancer is found in step (a) to be associated with cells in which the functional activity (e.g. expression) of SMARCB1 is low or absent or likely to be low or absent, identifying the patient as a cancer patient for whom administration of an inhibitor of the ubiquitin-proteasome system would be therapeutically beneficial.
(c) a method for determining whether a cancer patient or a subpopulation of cancer patients will therapeutically benefit or at least likely will benefit from the administration of an inhibitor of the ubiquitin-proteasome system:
  (i) determining whether the cancer present in a patient is associated with cells in which the functional activity of SMARCB1 is low or absent or likely to be low or absent; and
  (ii) where the cancer is found in step (a) to be associated with cells in which the functional activity of SMARCB1 is low or absent or likely to be low or absent, identifying the patient as a cancer patient for whom administration of an inhibitor of the ubiquitin-proteasome system will be or will likely be therapeutically beneficial; and where the cancer is found in step (a) to be associated with cells in which the functional activity of SMARCB1 is present and the level is not significantly lower than the level in a normal control, identifying the patient as a cancer patient for whom administration of an inhibitor of the ubiquitin-proteasome system is likely not to be therapeutically beneficial.

(d) a method for treating cancer in a patient having a cancer in which the functional activity SMARCB1 is low or absent or at least likely to be low or absent, the method comprising:
  (i) administering a therapeutically effective amount of an inhibitor of the ubiquitin-proteasome system to said patient.

(e) a method for treating cancer in a patient, the method comprising:
  (i) determining whether the cancer present in a patient is associated with cells in which the functional activity (e.g. expression) of SMARCB1 is low or absent or likely to be low or absent; and
  (ii) where the cancer is found in step (a) to be associated with cells in which the functional activity (e.g. expression) of SMARCB1 is low or absent or likely to be low or absent, administering to the patient an inhibitor of the ubiquitin-proteasome system.

(f) a method for identifying whether a patient suffering from cancer, which normally is treated with an inhibitor of the proteosome-ubiquitine system, would benefit of such treatment, the method comprising:
  (i) determining whether the cancer present in a patient is associated with cells in which the functional activity (e.g. expression) of SMARCB1 is low or absent or likely to be low or absent; and
  (ii) where the cancer is found in step (a) to be associated with cells in which the functional activity (e.g. expression) of SMARCB1 is low or absent or likely to be low or absent, administering to the patient an inhibitor of the ubiquitin-proteasome system.

(g) a method for identifying whether a patient suffering from cancer, which normally is treated with an inhibitor of the proteosome-ubiquitine system, would benefit of such treatment, the method comprising:
  (i) determining whether the cancer present in a patient is associated with cells in which the functional activity of SMARCB1 is low or absent or likely to be low or absent; and
  (ii) where the cancer is found in step (a) to be associated with cells in which the functional activity of SMARCB1 is low or absent or likely to be low or absent, identifying said patient as likely to benefit said treatment with an inhibitor of the proteosome-ubiquitine system; and where the cancer is found in step (a) to be associated with cells in which the functional activity of SMARCB1 is present and the level is not significantly lower than the level in a normal control, identifying said patient as not likely to benefit said treatment with an inhibitor of the proteosome-ubiquitine system.

The patient may have, or is suspected of having, a cancer selected from the group consisting of epithelioid sarcomas, synovial sarcomas, undifferentiated sarcomas without rhabdoid features, extraskeletal myxoid chondrosarcomas, Ewing sarcomas, mucinous carcinomas of the pancreas, malignant peripheral nerve sheath tumours, schwannomas, familial and sporadic schwannomatosis, cribriform neuroepithelial tumours, embryonal central nervous system tumours without rhabdoid features, choroid plexus carcinomas, teratoma, primitive neuroectodermal tumours (PNET), poorly differentiated chordomas, non-hodgkin lymphoma and chronic myeloid leukaemia, meningioma, glioblastoma, myoepithelial carcinoma, collecting duct carcinoma.

For example, the patient may have, or may be suspected of having, breast cancer.

The patient may have, or be suspected of having, malignant rhabdoid tumors, atypical teratoid/rhabdoid tumors, undifferentiated sarcomas with rhabdoid features, renal medullary carcinomas, embryonal central nervous system tumours with rhabdoid features, an atypical teratoid rhabdoid tumour (AT/RT) and/or a malignant rhabdoid tumour (MRT).

The above method aspects of the invention, step (i) comprises providing a sample of cells (e.g. cancer cells) from a patient and assessing the functional activity of SMARCB1 therein (as described above in relation to the first aspect of the invention. For example, the assessment of the patient may comprise measuring the amount of SMARCB1 protein in the cells, e.g. by immunohistochemistry, immunofluorescence, Western blot analysis, an immunological assay (e.g., an ELISA or other solid phase-based immunoassay such as SPRIA or amplified ELISA so called IMRAMP), a protein chip assay, surface-enhanced laser desorption/ionization (SELDI), high performance liquid chromatography, mass spectrometry, chemiluminescence, nephelometry/turbometry, lateral flow or pure or polarised fluorescence or electrophoresis.

Alternatively, or in addition, the assessment of the patient further may comprise measuring the amount of SMARCB1 mRNA, e.g. by quantitative PCR, digital PCR, Northern blot analysis, Next generation sequencing, SAGE, or array technologies.

Alternatively, or in addition, the assessment of the patient further may comprise determining the level of SMARCB1 activity (either directly or indirectly). Such activity may be assayed indirectly, for example by determining the genomic DNA, RNA or cDNA sequence, e.g. by fluorescence in situ hybridization, multiplex-ligation-dependent probe amplification, comparative genomic hybridization (CGH), array CGH, other array technologies, or sequencing techniques. Any DNA sequencing method (e.g. methods based on the Sanger method and ABI automated fluorescent sequencers, massively parallel sequencing/high-throughput sequencing/next-generation sequencing technologies) may be used to determine SMARCB1 mutations and genomic alterations (such as deletions).

The sequence information may then be used to identify chromosomal aberrations or DNA mutations that lead to a reduced or lost SMARCB1 activity. Alternatively, eIF2alpha phosphorylation and/or PP1 activity can be used as indirect markers of SMARCB1 activity.

Alternatively, or in addition, the assessment of the patient further may comprise determining epigenetic alterations (e.g. DNA methylation, histone modifications), that lead to low or absent SMARCB1 gene expression e.g. by DNA methylation analyses, chromatin immunoprecipitation-based techniques, mass spectrometry, chemical reactions (e.g. bisulfite treatment).

Step (i) may further comprise assessing the functional activity of SMARCB1 in one or more control samples of cells (which may include negative and/or positive controls; see above).

Step (i) may comprise assessing the functional activity of SMARCB1 in normal postnatal or prenatal tissue or cells from the patient as germline mutations have been found in patients with familial or sporadic tumours (see for example Sevenet et al., 1999, *Am J Human Genet.* 65, 1342-8; Eaton et al., 2011; *Pediatr Blood Cancer* 56, 7-15; Bourdeaut et al., 2011; *Clin Cancer Res* 17, 31-8; van den Munckhof et al., 2012; *Neurogenetics* 13, 1-7).

Step (i) may also comprise diagnosing the type of cancer from which the patient is suffering.

The inhibitor of the ubiquitin-proteasome system is a proteasome inhibitor selected from the group consisting of bortezomib (PS-341, MG-341, Velcade®), PI-083, MLN 9708, MLN 4924, MLN 519, Carfilzomib, ONX 0912, CEP-1877, NPI-0052, BU-32 (NSC D750499-S), PR-171, IPSI-001, and natural products with proteasome-inhibitory effects, such as green tea polyphenol (−)-epigallocatechin-3-gallate (EGCG), soy isoflavone genistein, and the spice turmeric compound curcumin.

For example, the inhibitor of the ubiquitin-proteasome system may be bortezomib or Carfilzomib.

Preferred administration regimes for the inhibitor of the ubiquitin-proteasome system are detailed above in relation to the first aspect of the invention.

The inhibitors mentioned in the tables herein as well as all other details regarding the inhibitors are also relevant for the method and other aspects of the present invention.

For example, the inhibitor of the ubiquitin-proteasome system may be for administration by a route selected from the group consisting of parenteral, intratumoral, oral, intravenous, transdermal and intramuscular routes.

Likewise, the inhibitor of the ubiquitin-proteasome system may be administered at a dose of between 0.5 to 100 mg/m$^2$ per dose such as 0.5 to 1.3 mg/m$^2$, which may be repeated at regular intervals (for example daily, twice weekly, weekly, bi-weekly, monthly, etc).

The patient may also receive one or more further treatments for the treatment of cancer, such as an additional pharmaceutical agent (such as a chemotherapeutic agent), radiotherapy and/or surgery (see above).

A further aspect of the present invention relates to an inhibitor of the ubiquitin-proteasome system for use in treating cancer in a patient, wherein the patient is assessed to establish that the cancer is associated with cells in which the functional activity of SMARCB1 is low or absent.

In one embodiment the patient has, or is suspected of having, a cancer selected from the group consisting of malignant rhabdoid tumors, atypical teratoid/rhabdoid tumors, epithelioid sarcomas, synovial sarcomas, undifferentiated sarcomas without rhabdoid features, extraskeletal myxoid chondrosarcomas, mucinous carcinomas of the pancreas, malignant peripheral nerve sheath tumours, schwannomas, familial and sporadic schwannomatosis, cribriform neuroepithelial tumours, embryonal central nervous system tumours without rhabdoid features, choroid plexus carcinomas, teratoma, primitive neuroectodermal tumours, poorly differentiated chordomas, non-hodgkin lymphoma, and chronic myeloid leukaemia, meningioma, glioblastoma, myoepithelial carcinoma, collecting duct carcinoma. In a further embodiment, the patient has, or is suspected of having, breast cancer.

In another embodiment of the present invention, the inhibitor is for use in the treatment of a patient having, or is suspected of having, an atypical teratoid rhabdoid tumour (AT/RT) and/or a malignant rhabdoid tumour (MRT), an undifferentiated sarcoma with rhabdoid features, renal medullary carcinomas, or embryonal central nervous system tumours with rhabdoid features.

The patient may be or have been assessed prior to commencement of treatment with the inhibitor. The assessment may comprises providing a sample of cells from a patient and assessing the functional activity of SMARCB1 therein. The cells of the sample may be cancer cells or predominantly cancer cells.

The assessment may be done by determining the functional activity of SMARCB1 comprises measuring the amount of SMARCB1 protein, and/or mRNA encoding the same, in the cells. The assessment may be done by determining the functional activity of SMARCB1 comprises determining the SMARCB1 genomic DNA or cDNA sequence. In one embodiment the assessment of the patient further comprises assessing the functional activity of SMARCB1 in one or more control samples of cells, for example one or more control samples of cells comprising negative control samples.

In a further embodiment, the inhibitor for use according to the present invention, the assessment of the patient comprises diagnosing the type of cancer from which the patient is suffering.

In a preferred embodiment of the present invention, the inhibitor is an inhibitor of the ubiquitin-proteasome system such as a proteasome inhibitor selected from the group consisting of bortezomib (PS-341, MG-341, Velcade®), PI-083, MLN 9708, MLN 4924, MLN 519, Carfilzomib, ONX 0912, CEP-1877, NPI-0052. BU-32 (NSC D750499-S), PR-171, IPSI-001, and natural products with proteasome-inhibitory effects, such as green tea polyphenol (−)-epigallocatechin-3-gallate (EGCG), soy isoflavone genistein, and the spice turmeric compound curcumin. In yet a preferred embodiment, the proteasome inhibitor is bortezomib.

In another embodiment, the inhibitor is for administration by a route selected from the group consisting of parenteral, intratumoral, oral, intravenous, transdermal and intramuscular routes. In a further embodiment, the proteasome inhibitor is for administration at a dose of between 0.5 to 100 mg/m$^2$ per dose such as 0.5 to 1.3 mg/m$^2$ per dose.

In yet a further embodiment, the patient also receives one or more further treatments for cancer. Where the patient receives one or more further treatment, the one or more further treatments may be selected from the group consisting of conventional chemotherapeutic agents (such as alkylating agents, anti-metabolites, plant alkaloids and terpenoids, topoisomerase inhibitors and antineoplastics), radiotherapeutic agents, antibody-based therapeutic agents (such as gemtuzumab, alemtuzumab, rituximab, trastuzumab, nimotuzumab, cetuximab, bevacizumab), and steroids.

Yet a further aspect concerns the use of an inhibitor of the ubiquitin-proteasome system in the preparation of a medicament for treating cancer in a patient, wherein the patient is assessed to establish that the cancer is associated with cells in which the functional activity of SMARCB1 is low or absent. The patient is assessed prior to treatment, with an inhibitor of the ubiquitin-proteasome system. The inhibitor of the ubiquitin-proteasome system used to establish that the cancer is associated with cells in which the functional activity of SMARCB is low or absent may be the same or different as the inhibitor of the ubiquitin-proteasome system in the preparation of a medicament.

Preferred, non-limiting examples which embody certain aspects of the invention will now be described, with reference to the following figure:

FIG. 1: Involvement of SMARCB1 in the Unfolded Protein Response (UPR)

A, shRNA-mediated SMARCB1 knock-down in MCF7 cells (tetracycline-induced) leads to increased eIF2alpha phosphorylation as determined by immunoblots. ER stress was induced by DTT and thapsigargin (TG) treatment for three hours. Unconventional splicing of XBP1 is shown by RT-PCR as an indicator of another activated UPR branch. XBP1s, XBP1u, XBP1h: spliced, unspliced and hybrid XBP1 cDNA (the latter representing XBP1s/XBP1u heterodimers).

B, Schematic summary showing the connection between SMARCB1 and eIF2alpha phosphorylation.

C, Increased eIF2alpha phosphorylation levels upon three hour TG exposure are detected in the human AT/RT cell line CHLA2 and the human MRT cell lines LM (liver origin), A-204 (muscle origin), and G401 (kidney origin), all of which lacking SMARCB1, in comparison to human SMARCB1-positive brain tumor (DAOY, SW1783, Hs683), renal cell carcinoma (786-O, A-498) and hepatocellular carcinoma (HepG2) cell lines. Fold-change of β-actin-normalized phosphorylated eIF2alpha signal intensities between TSG-treated and untreated cells: CHLA2: 5.89; LM: 1.27; A-204: 1.39; G401: 2.49; DAOY: 0.77; SW1783: 0.75; Hs683: 0.81; 786-O: 0.60; A-498: 1.12; HepG2: 0.56.

D, SMARCB1 is present in the nucleus of 786-O cells and co-localizes with the ER marker calnexin in the cytoplasm.

E, Treatment of MCF7 cells with 10 nM of the proteasome inhibitor Bortezomib (BTZ) for 12 hours leads to increased apoptosis in tetracycline (Tet)-induced SMARCB1 knock-down (kd) cells. Percentages of Annexin V-positive and 7AAD-negative apoptotic cells of three independent experiments are shown. Error bars: standard error of the mean. P-values of unpaired t-tests comparing non-induced to Tet-induced cells.

F, Treatment of SMARCB1-positive renal cell carcinoma (786-O, A-498) and brain tumor (SW1783, DAOY) cells, a kidney MRT (G401) and a brain AT/RT (BT12) cell line with 10 nM BTZ for 24 hours leads to highest apoptosis in the rhabdoid tumor cells G401 and BT12 compared to DMSO (vehicle)-treated cells. The kidney and brain tumor cell lines were kept under comparable adherent culture conditions, respectively. Percentages of Annexin V-positive and 7AAD-negative apoptotic cells of three independent experiments are shown. Error bars: standard error of the mean. P-values of unpaired t-tests comparing BTZ to DMSO-treated cells.

Figure 2:
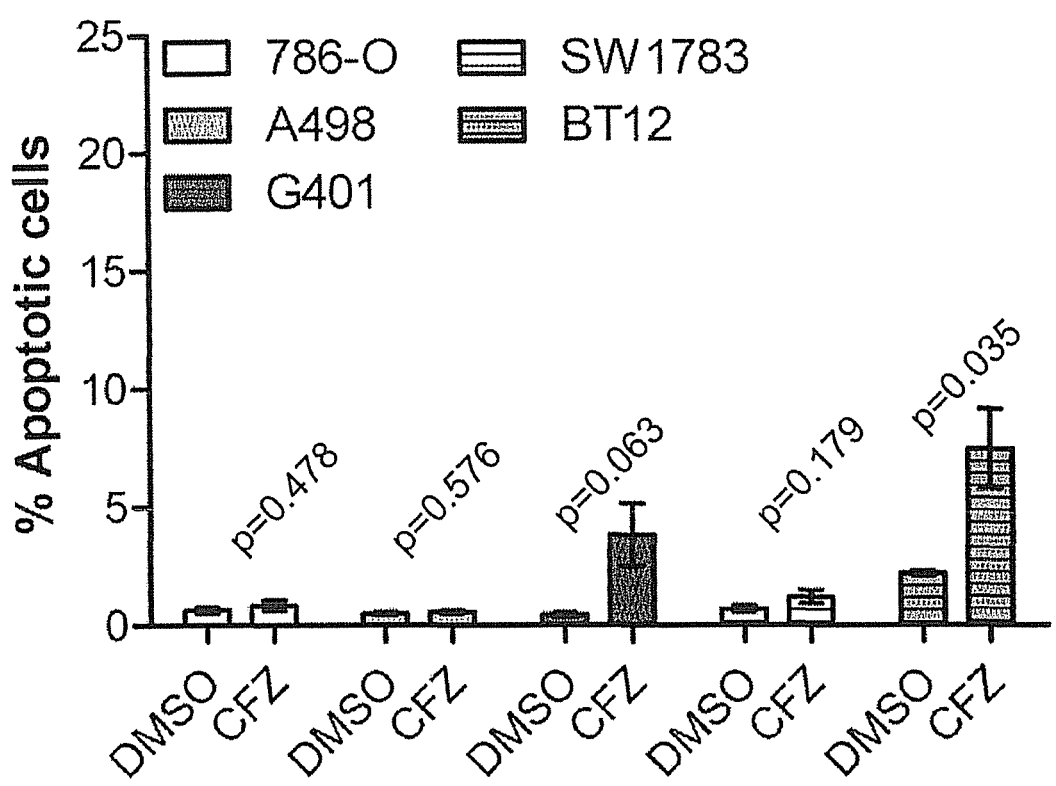
FIG. 2 shows the treatment of SMARCB1-positive cell lines with Carfilzomib.

FIG. 2: Treatment with Another Proteasome Inhibitor (Carfilzomib)

Treatment of SMARCB1-positive renal cell carcinoma (786-O, A-498) and brain tumor (SW1783) cells, a kidney MRT (G401) and a brain AT/RT (BT12) cell line with 30 nM Carfilzomib (CFZ) for 24 hours leads to highest apoptosis in the rhabdoid tumor cells G401 and BT12 compared to DMSO (vehicle)-treated cells. The kidney and brain tumor cell lines were kept under comparable adherent culture conditions, respectively. Percentages of Annexin V-positive and 7AAD-negative apoptotic cells of three independent experiments are shown. Error bars: standard error of the mean. P-values of unpaired t-tests comparing CFZ to DMSO-treated cells.

EXAMPLES

Introduction

SMARCB1 is a tumor suppressor whose function is lost in diverse tumor types, including malignant rhabdoid tumors of different organs. In most of these cases, biallelic inactivation of SMARCB1 leads to a complete loss of the protein. We found that reduced cellular SMARCB1 levels are associated with the activation of the unfolded protein response. Specifically, such cells display an increased sensitivity toward phosphorylation of eIF2alpha (alpha subunit of the eukaryotic translation initiation factor 2), a central component of the unfolded protein response.

Sustained eIF2alpha phosphorylation has been shown to confer cytoprotection against hypoxia, oxidative stress, and long term glucose deficiency, all of which represent typical in vivo conditions of rapidly growing tumors (Bi et al., 2005; Harding et al., 2003; Koumenis et al., 2002; Muaddi et al., 2010; Wiseman and Balch, 2005).

We demonstrate that the consequences of loss-of-function of SMARCB1 may be therapeutically exploited: Inhibition of the degradation of unfolded proteins by certain compounds, including proteasome inhibitors, leads to increased apoptosis of cells with reduced or lost SMARCB1 function. The proteasome is a multicatalytic enzyme which degrades proteins that are marked for destruction by ubiquitin tags. Degradation of proteins can be blocked by inhibiting the tagging of proteins with ubiquitin residues, by modulating de-ubiquitination, or by inhibiting proteasome activity itself.

Materials & Methods

Western Blot Analysis

Cells were harvested at 50-70% confluency, pelleted by centrifugation, and dissolved in RIPA buffer (10 mM Tris/HCl (pH 7.5), 1 mM EDTA, 1% Triton X-100, 0.1% SDS, 0.1% sodium deoxycholate, 100 mM NaCl) supplemented with protease inhibitors (2 mM PMSF and 1× Complete Mini, Roche). Supernatants were collected, protein concentrations were determined using the BCA assay (Pierce/Thermo Scientific), and proteins were separated in a 10% SDS-polyacrylamide gel. Western blotting followed standard protocols using nitrocellulose membranes (Amersham/GE Healthcare). Signal intensities were analyzed with ImageJ (http://rsb.info.nih.gov/ij/).

Antibodies used were: anti-BAF47 (SMARCB1/SNF5; BD Biosciences, San Diego, Calif.), anti-phospho-eIF2alpha (119A11; Cell Signaling), anti-beta actin-HRP (Abcam, Cambridge, UK).

Culture of Human Cell Lines

The CHLA-02-ATRT cell line was obtained from ATCC and kept in neurosphere medium (DMEM/F12 (1:1) with Glutamax, B27, penicillin (100 units/mL), streptomycin (100 µg/mL; all from Invitrogen), HEPES (10 mmol/L), Partricin (0.5 µg/mL, Biochrom); insulin (20 µg/mL; Sigma Aldrich), recombinant human epidermal growth factor (EGF; 20 ng/mL), and rhFGFbasic (20 ng/mL; PAN Biotech)). The human malignant rhabdoid tumor cell line LM (provided by Rupert Handgretinger, Tuebingen, Germany) was kept according to Versteege et al. (Nature 1998). DAOY medulloblastoma cells (provided by Michael Grotzer, Zurich, Switzerland) were kept in EMEM (PAA) supplemented with 10% FBS (Biochrom), 2 mM glutamine, 100 units/mL Penicillin/Streptomycin (Invitrogen), and 2.5 µg/mL Amphotericin B (PAA). Hs683 glioma cell lines (provided by Matthias Simon, Bonn, Germany) were kept in DAOY medium with 1 mM sodium pyruvate, MEM non-essential amino acids, and MEM vitamin solution (all from Invitrogen). SW1783 glioblastoma cells (provided by Matthias Simon, Bonn, Germany) and BT12 AT/RT cells (provided by Michael Grotzer, Zurich, Switzerland) were kept in DMEM (1 g/l glucose) supplemented with 10% FBS (Biochrom), 2 mM glutamine, 100 units/ml Penicillin/Streptomycin (Invitrogen) and 2.5 µg/ml Amphotericin B (PAA).

MCF7-SNF5-KD#73 cells (Xu et al., 2010) were cultured in DMEM (4.5 g/L glucose, Invitrogen), 10% FBS (Tet System Approved, Clontech), 2 mM glutamine, and 100 units/mL Penicillin/Streptomycin (Invitrogen). For the knock-down of SMARCB1, tetracycline (1 µg/mL) was added on day 1 and 3, and cells harvested at day 4. At day 4, cells were treated with DTT (5 mM) or Thapsigargin (5 µM). 786-O and A-498 cells (both from Angelika Toelle, Charité Berlin, Germany), HepG2 cells (from Peter Nilsson-Ehle, Lund University, Sweden), and G401 (ATCC) were kept in RPMI1640 (PAA) supplemented with 10% FBS (Biochrom), 2 mM glutamine, 100 units/mL Penicillin/Streptomycin (Invitrogen), and 2.5 µg/mL Amphotericin B (PAA). A-204 (ATCC) were grown in McCoy's 5a modified medium supplemented with 10% FBS (Biochrom), 100 units/mL Penicillin/Streptomycin (Invitrogen), and 2.5 µg/mL Amphotericin B (PAA). All cells were kept in T75 tissue culture flasks (Techno Plastic Products).

Immunofluorescence

Coverslips with attached cells were treated with Triton X-100 (0.1% in PBS) for 10 min, washed with PBS three times (10 min each), and incubated with primary antibodies at 4° C. overnight. PBS without primary antibody was used as a negative control. Before a one hour RT incubation with secondary antibodies (coupled to Cy3 (Jackson ImmunoResearch) and Alexa 488 (Invitrogen)), three 15 min washing steps in PBS were performed followed by the application of 5% donkey serum in PBS for 30 min at RT. Specimens were then washed three times in PBS (15 min each), rinsed briefly in water, dehydrated in ethanol, and air dried. A mounting medium containing 4',6'-diamidino-2-phenylindole (DAPI) nuclear stain was used.

The following primary antibodies were used: anti-BAF47 (SMARCB1/SNF5; 1:100; BD Biosciences, San Diego, Calif.), anti-Calnexin (1:100; C5C9; Cell Signaling Technology). Images of cells on coverslips were taken with an Axiovert 200M microscope using AxioVision 4.5 software (Zeiss).

Apoptosis Assay 500,000 MCF7-SNF5-KD#73 cells (Xu et al., 2010) were plated into T75 tissue culture flasks (Techno Plastic Products). For knockdown experiments, tetracycline (1 µg/mL) was added on day 1 and day 3. In case of Bortezomib (BTZ)-treated cells, the drug (Santa Cruz Biotechnology, final concentration 10 nM) was added for 12 hours on day 4 (at 70-85% confluency).

Similarly, G401, A498, 786-O, BT12, SW1783, and DAOY cells were plated into 6-well-plates (200,000 cells per well) and grown for 24 hours before 10 nM BTZ, 30 nM Carfilzomib (CFZ, from Active Biochemicals Co.), or DMSO as vehicle control was added to the cell culture media for another 24 hours. Subsequently, cells were carefully washed with PBS and dissociated by trypsinization. Aliquots of single cell suspensions containing $1 \times 10^5$ cells in 100 µL PBS were stained with AnnexinV-APC and 7AAD according to the manufacturer's instructions (BD Biosciences) for 15 min at RT. Subsequently, 400 µL of AnnexinV binding buffer was added (10 mM Hepes, 140 mM NaCl and 2.5 mM $CaCl_2$), cell suspensions were placed on ice and immediately analyzed with a FACSCalibur flow cytometer (BD Biosciences). The data analysis was performed using the FlowJo software (Tree Star). For statistical analyses, an unpaired t-test was conducted using Prism 5.0 (GraphPad).

Results

An involvement of the unfolded protein response (UPR) in cerebral and extracerebral malignant rhabdoid tumour biology has not previously been reported. Using an MCF7 breast cancer cell line, in which SMARCB1 knockdown can be induced by tetracycline (Xu et al., 2010), we found an increased phosphorylation of eIF2alpha upon SMARCB1 reduction (FIG. 1A).

Elevated eIF2alpha phosphorylation levels were also detected upon Thapsigargin-mediated ER stress induction in human SMARCB1-negative tumour cell lines in comparison to human SMARCB1-positive brain tumour cells lines (FIG. 1C).

EIF2alpha is a central component of one of the three UPR branches and can be phosphorylated by four different kinases (PERK; GCN2, HRI, PKR) (FIG. 1B). The reverse reaction, dephosphorylation of eIF2alpha, is performed by the catalytic subunit of protein phosphatase-1 (PP1c).

SMARCB1 has previously been reported to bind to the catalytic subunit of PP1 (PP1c) and to the PP1 regulatory subunit 15 (PPP1R15A/GADD34), and was shown to increase PP1c activity in solution (Wu et al., 2002). Thus, a likely explanation for increased eIF2alpha phosphorylation in SMARCB1 knockdown cells is a diminished PP1c activity.

Immunostainings revealed that SMARCB1 is not only present in the nucleus, but also co-localized with the ER marker calnexin in the cytoplasm (FIG. 1D).

Since phosphorylation of eIF2alpha is known to enhance apoptosis in combination with proteasome inhibition, we tested if the over-activation of the eIF2alpha branch could be therapeutically exploited. Treatment with the proteasome inhibitor Bortezomib resulted in increased apoptosis of MCF7-SMARCB1 knock-down cells, a kidney MRT and a brain AT/RT cell line in comparison to SMARCB1-expressing control cells (FIGS. 1E and F). An increased apoptosis was also detected in the kidney MRT and brain AT/RT line upon treatment with another proteasome inhibitor, Carfilzomib (FIG. 2).

Discussion

The experimental results suggest that reduced levels of SMARCB1 protein, which has previously been shown to activate PP1c-GADD34 in solution (Wu et al., 2002), accounts for an elevated cellular sensitivity toward eIF2alpha phosphorylation, a central UPR mechanism (FIG. 1). In contrast to acute eIF2alpha phosphorylation, which can be pro-apoptotic, sustained eIF2alpha phosphorylation has been shown to confer cytoprotection against hypoxia, oxidative stress, and long term glucose deficiency, all of which representing typical in vivo conditions of rapidly growing tumors ((Koumenis et al., 2002); (Harding et al., 2003); (Bi et al., 2005); (Wiseman and Balch, 2005); (Muaddi et al., 2010)). Here we show that reduced or absent levels of the tumor suppressor SMARCB1 result in a cellular state which is characterized by an elevated sensitivity toward eIF2alpha phosphorylation. Importantly, we demonstrate that the involvement of SMARCB1 in regulating the UPR may be therapeutically exploited: Application of the proteasome inhibitors Carfilzomib and Bortezomib, the latter known to synergize with a chemical inhibitor of the GADD34-PP1c complex (Schewe and Aguirre-Ghiso, 2009), leads to apoptosis of cells with reduced SMARCB1 levels (FIGS. 1 and 2). Such an approach represents a novel strategy for treating tumours with reduced or lost SMARCB1 function.

Example of determination of reduced or absent SMARCB1 protein in diverse tissue samples by immunostaining.

SMARCB1 protein levels are detected by immunostaining, which is a sequential procedure with several steps involving first the application of a specific primary antibody recognizing SMARCB1 (for example INI1/BAF47 antibody from BD Transduction Laboratories) followed by a secondary antibody which is conjugated to a fluorophore (immunofluorescence staining) or an enzyme (immunohistochemistry). In case of the latter, a chromogenic substrate is added for detection. Enzymatic activation of the chromogenic substrate creates a visible product. The sample is washed between each step. The results are interpreted using a fluorescence microscope (in case of immunofluorescence staining), or light microscope or scanner (in case of immunohistochemistry). The detection can be done both manually and with automated immunostainers. Staining of normal cells, for example blood vessel and stroma cells within the same tissue section can serve as an internal reference for cells with reduced or absent SMARCB1.

A.1 Formalin-Fixed, Paraffin-Embedded Tissue

5-μm histological sections of formalin-fixed, paraffin-embedded tissue are deparaffinized and rehydrated through alcohol by the following steps:
  2×5 min in TissueClear (HistoLab)
  2×10 min 100% EtOH
  1×5 min 70% EtOH
  1×5 min 50% EtOH
  1 min $H_2O$ Epitope retrieval may or may not be performed:

Incubation of slides in 95-100° C. preheated citrate buffer (10 mM sodium citrate, 0.05% Tween-20, pH 6.0) for 20 min Incubation of slides in citrate buffer (10 mM sodium citrate, 0.05% Tween-20, pH 6.0) for 20 min at room temperature Instead of a water bath, a microwave can be applied to heat the citrate buffer PBS Wash In case of immunohistochemistry, endogenous peroxidase is blocked with hydrogen peroxide (0.35% $H_2O_2$ in $H_2O$) for 20 min 3× wash in PBS Optional block with 5% donkey serum/PBS 60 min at room temperature Primary antibody (e.g. BAF47 antibody from BD Transduction Laboratories, cat. no. 612110), is used in a dilution of 1:25 to 1:1000 in PBS Primary antibody incubation over night at 4° C. or 1 hour at room temperature
  3× wash in PBS 5 min each Incubation of secondary antibody (dilution 1:200-1:1000 in 5% donkey serum) for 2 h at room temperature. Secondary antibody in case of enzymatic detection, for example: HRP-coupled anti mouse antibody. Secondary antibody in case of immunofluorescence staining, for example:
  Cy3-coupled anti mouse antibody.
  3× wash in PBS for 5 min each.

Final embedding in case of immunofluorescence staining at this step.

In case of HRP-coupled secondary antibody:
DAB incubation, hematoxylin counterstaining, dehydration and embedding:
  ABC reagent incubation for 30 min at room temperature (R.T.U. VectaStain ABC, cat. no. PK7100)
  3×5 min incubation in PBS
  Incubation 1 min $H_2O$
  Preparation of DAB solution: (Vector DAB substrate, cat. no. SK4100)
  2.5 mL destilled $H_2O$
  +1 drop buffer
  +2 drops DAB substrate
  +1 drop $H_2O_2$ solution
  Incubation in DAB working solution for 2-10 min
  Use the microscope to check for a good staining versus background ratio
  Wash in $H_2O$ for 5 min at RT
  Harris Haematoxylin (filtrate daily before use): about 60 sec incubation
  $H_2O$: dip up and down 10 times
  $H_2O$: dip until excess haematoxylin is removed—the slide around the tissue should be clear of haematoxylin
  0.5% acid alcohol, 1 quick dip
  $H_2O$: dip 10 times
  $H_2O$: dip 10 times
  Bicarbonate solution, 30 sec
  $H_2O$: dip 15 times
  80% EtOH
  100% EtOH—10 dips, then incubate 1 min
  100% EtOH—10 dips then incubate 1 min
  Xylene—10 dips
  Xylene—10 dips
  Embed with Entellan mounting medium Otherwise follow standard procedure and the recommendations given by the manufacturer for the primary and secondary antibodies used. In the case of using automated immunostainers, use the specified buffers and materials for each instrument.

A.2 Cryosections

In case of cryosections, no deparaffinization/rehydration and no epitope retrieval are performed.

REFERENCES

Bourdeaut F, Lequin D, Brugières L, Reynaud S, Dufour C, Doz F, André N, Stephan J L, Pérel Y, Oberlin O, Orbach D, Bergeron C, Rialland X, Fréneaux P, Ranchere D, Figarella-Branger D, Audry G, Puget S, Evans D G, Pinas J C, Capra V, Mosseri V, Coupier I, Gauthier-Villars M, Pierron G, Delattre O (2011). Frequent hSNF5/INI1 germline mutations in patients with rhabdoid tumor. Clin Cancer Res. 1, 31-8.

Bi, M., Naczki, C., Koritzinsky, M., Fels, D., Blais, J., Hu, N., Harding, H., Novoa, I., Varia, M., Raleigh, J., et al. (2005). ER stress-regulated translation increases tolerance to extreme hypoxia and promotes tumor growth. EMBO J 24, 3470-3481.

Harding, H. P., Zhang, Y., Zeng, H., Novoa, I., Lu, P. D., Calfon, M., Sadri, N., Yun, C., Popko, B., Paules, R., et al. (2003). An integrated stress response regulates amino acid metabolism and resistance to oxidative stress. Mol Cell 11, 619-633.

Koumenis, C., Naczki, C., Koritzinsky, M., Rastani, S., Diehl, A., Sonenberg, N., Koromilas, A., and Wouters, B. G. (2002). Regulation of protein synthesis by hypoxia via activation of the endoplasmic reticulum kinase PERK and phosphorylation of the translation initiation factor eIF2alpha. Mol Cell Biol 22, 7405-7416.

Muaddi, H., Majumder, M., Peidis, P., Papadakis, A. I., Holcik, M., Scheuner, D., Kaufman, R. J., Hatzoglou, M., and Koromilas, A. E. (2010). Phosphorylation of eIF2alpha at serine 51 is an important determinant of cell survival and adaptation to glucose deficiency. Mol Biol Cell 21, 3220-3231.

Schewe, D. M., and Aguirre-Ghiso, J. A. (2009). Inhibition of eIF2alpha dephosphorylation maximizes bortezomib efficiency and eliminates quiescent multiple myeloma cells surviving proteasome inhibitor therapy. Cancer Res 69, 1545-1552.

van den Munckhof P, Christiaans I, Kenter S B, Baas F, Hulsebos T J. (2012) Germline SMARCB1 mutation predisposes to multiple meningiomas and schwannomas with preferential location of cranial meningiomas at the falx cerebri. Neurogenetics 13, 1-7.

Versteege, I., Sevenet, N., Lange, J., Rousseau-Merck, M. F., Ambros, P., Handgretinger, R., Aurias, A., and Delattre, O. (1998). Truncating mutations of hSNF5/INI1 in aggressive paediatric cancer. Nature 394, 203-206.

Wiseman, R. L., and Balch, W. E. (2005). A new pharmacology—drugging stressed folding pathways. Trends Mol Med 11, 347-350.

Wu, D. Y., Tkachuck, D. C., Roberson, R. S., and Schubach, W. H. (2002). The human SNF5/INI1 protein facilitates the function of the growth arrest and DNA damage-inducible protein (GADD34) and modulates GADD34-bound protein phosphatase-1 activity. J Biol Chem 277, 27706-27715.

Xu, Y., Yan, W., and Chen, X. (2010). SNF5, a core component of the SWI/SNF complex, is necessary for p53 expression and cell survival, in part through eIF4E. Oncogene 29, 4090-4100.

The invention claimed is:

1. A method for selecting a pharmaceutical agent for treating cancer in a patient, the method comprising:
   a. determining whether the cancer present in a patient is associated with cells in which the functional activity of SMARCB1 is low or absent;
   b. where the cancer is found in step (a) to be associated with cells in which the functional activity of SMARCB1 is low or absent, selecting an inhibitor of the ubiquitin-proteasome system as a pharmaceutical agent for treating cancer in the patient and
   c. administering the selected inhibitor of the ubiquitin-proteasome system to the patient,
   wherein the cancer is selected from the group consisting of malignant rhabdoid tumors, atypical teratoid/rhabdoid tumors, epithelioid sarcomas, synovial sarcomas, undifferentiated sarcomas with or without rhabdoid features, extraskeletal myxoid chondrosarcomas, schwannomas, familial and sporadic schwannomatosis, cribriform neuroepithelial tumours, choroid plexus carcinomas, teratomas, primitive neuroectodermal tumours, and myoepithelial carcinomas.

2. A method for identifying a cancer patient for whom administration of an inhibitor of the ubiquitin-proteasome system would be therapeutically beneficial, the method comprising:
   a. determining whether the cancer present in a patient is associated with cells in which the functional activity of SMARCB1 is low or absent;
   b. where the cancer is found in step (a) to be associated with cells in which the functional activity of SMARCB1 is low or absent, identifying the patient as a cancer patient for whom administration of an inhibitor of the ubiquitin-proteasome system would be therapeutically beneficial; and
   c. administering an inhibitor of the ubiquitin-proteasome system to said patient,
   wherein the cancer is selected from the group consisting of malignant rhabdoid tumors, atypical teratoid/rhabdoid tumors, epithelioid sarcomas, synovial sarcomas, undifferentiated sarcomas with or without rhabdoid features, extraskeletal myxoid chondrosarcomas, schwannomas, familial and sporadic schwannomatosis, cribriform neuroepithelial tumours, choroid plexus carcinomas, teratomas, primitive neuroectodermal tumours, and myoepithelial carcinomas.

3. A method for determining whether a cancer patient will therapeutically benefit or at least likely will benefit from the administration of an inhibitor of the ubiquitin-proteasome system:
   a. determining whether the cancer present in a patient is associated with cells in which the functional activity of SMARCB1 is low or absent or likely to be low or absent;
   b. where the cancer is found in step (a) to be associated with cells in which the functional activity of SMARCB1 is low or absent or likely to be low or absent, identifying the patient as a cancer patient for whom administration of an inhibitor of the ubiquitin-proteasome system will be or will likely be therapeutically beneficial, and administering an inhibitor of the ubiquitin-proteasome system to said patient; and
   where the cancer is found in step (a) to be associated with cells in which the functional activity of SMARCB1 is present and the level is not significantly lower than the level in a normal control, identifying the patient as a cancer patient for whom administration of an inhibitor of the ubiquitin-proteasome system is likely not to be therapeutically beneficial,
   wherein the cancer is selected from the group consisting of malignant rhabdoid tumors, atypical teratoid/rhabdoid tumors, epithelioid sarcomas, synovial sarcomas, undifferentiated sarcomas with or without rhabdoid features, extraskeletal myxoid chondrosarcomas, schwannomas, familial and sporadic schwannomatosis, cribriform neuroepithelial tumours, choroid plexus carcinomas, teratomas, primitive neuroectodermal tumours, and myoepithelial carcinomas.

4. A method for treating cancer in a patient having a cancer in which the functional activity of SMARCB1 is low or absent or likely to be low or absent, the method comprising administering to said patient an amount of an inhibitor of the ubiquitin-proteasome system that is effective to treat said cancer, wherein said cancer is selected from the group consisting of malignant rhabdoid tumors, atypical teratoid/rhabdoid tumors, epithelioid sarcomas, synovial sarcomas, undifferentiated sarcomas with or without rhabdoid features, extraskeletal myxoid chondrosarcomas, schwannomas, familial and sporadic schwannomatosis, cribriform neuroepithelial tumours, choroid plexus carcinomas, teratomas, primitive neuroectodermal tumours, and myoepithelial carcinomas.

5. A method for treating cancer in a patient, the method comprising:
   a. determining whether the cancer present in a patient is associated with cells in which the functional activity of SMARCB1 is low or absent; and
   b. where the cancer is found in step (a) to be associated with cells in which the functional activity of SMARCB1 is low or absent, administering to the patient an amount of an inhibitor of the ubiquitin-proteasome system that is effective to treat said cancer,
   wherein said cancer is selected from the group consisting of malignant rhabdoid tumors, atypical teratoid/rhabdoid tumors, epithelioid sarcomas, synovial sarcomas, undifferentiated sarcomas with or without rhabdoid features, extraskeletal myxoid chondrosarcomas, schwannomas, familial and sporadic schwannomatosis, cribriform neuroepithelial tumours, choroid plexus carcinomas, teratomas, primitive neuroectodermal tumours, and myoepithelial carcinomas.

6. A method according to claim 5 wherein the patient has, or is suspected of having an atypical teratoid rhabdoid tumour (AT/RT) and/or a malignant rhabdoid tumour (MRT).

7. A method according to claim 5, wherein step (a) comprises providing a sample of cells from a patient and assessing the functional activity of SMARCB1 therein.

8. A method according to claim 7 wherein the cells are cancer cells.

9. A method according to claim 7 wherein step (a) comprises measuring the amount of SMARCB1 protein in the cells.

10. A method according to claim 7 wherein step (a) comprises measuring the amount of SMARCB1 mRNA or cDNA in the cells.

11. A method according to claim 7 wherein step (a) comprises assessing the SMARCB1 genomic DNA or cDNA sequence.

12. A method according to claim 7 wherein step (a) further comprises assessing the functional activity of SMARCB1 in one or more control samples of cells.

13. A method according to claim 12 wherein the one or more control samples of cells comprise negative control samples.

14. A method according to claim 12 wherein the one or more control samples of cells comprise positive control samples.

15. A method according to claim 5, wherein step (a) comprises diagnosing the type of cancer from which the patient is suffering.

16. A method according to claim 5, wherein the inhibitor of the ubiquitin-proteasome system is a proteasome inhibitor selected from the group consisting of bortezomib (PS-341, MG-341, Velcade®), PI-083, MLN 9708, MLN 4924, MLN 519, carfilzomib, ONX 0912, CEP-1877, NPI-0052, BU-32 (NSC D750499-S), PR-171, IPSI-001, and natural products with proteasome-inhibitory effects.

17. A method according to claim 5 wherein the proteasome inhibitor is bortezomib.

18. A method according to claim 5 wherein the proteasome inhibitor is carfilzomib.

19. A method according to claim 5 wherein the proteasome inhibitor is for administration administered by a route selected from the group consisting of parenteral, intratumoral, oral, intravenous, transdermal and intramuscular routes.

20. A method according to claim 5, wherein the proteasome inhibitor is administered at a dose of between 0.5 to 100 mg/m2 per dose such as 0.5 to 1.3 mg/m2 per dose.

21. A method according to claim 5, wherein the patient also receives one or more further treatments for cancer.

22. A method according to claim 21 wherein the one or more further treatments are selected from the group consisting of conventional chemotherapeutic agents, radiotherapeutic agents, antibody-based therapeutic agents, and steroids.

23. A method according to claim 5, wherein the inhibitor of the ubiquitin-proteasome system is a proteasome inhibitor selected from the group consisting of green tea polyphenol (−) epigallocatechin-3-gallate (EGCG), soy isoflavone genistein, and the spice turmeric compound curcumin.

24. A method according to claim 5, wherein the proteasome inhibitor is administered at a dose of between 0.5 to 1.3 mg/m2 per dose.

25. A method according to claim 22, wherein the conventional chemotherapeutic agents are selected from the group consisting of alkylating agents, anti-metabolites, plant alkaloids and terpenoids, topoisomerase inhibitors and antineoplastics.

26. A method according to claim 22, wherein the antibody-based therapeutic agents are selected from the group consisting of gemtuzumab, alemtuzumab, rituximab, trastuzumab, nimotuzumab, cetuximab, and bevacizumab.

* * * * *